(12) United States Patent
Kamei

(10) Patent No.: US 8,912,354 B2
(45) Date of Patent: Dec. 16, 2014

(54) ORGANOPOLYSILOXANE AND COSMETIC CONTAINING THE SAME

(75) Inventor: Masanao Kamei, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 663 days.

(21) Appl. No.: 13/182,036

(22) Filed: Jul. 13, 2011

(65) Prior Publication Data

US 2012/0040931 A1 Feb. 16, 2012

(30) Foreign Application Priority Data

Aug. 11, 2010 (JP) ................................ 2010-180421

(51) Int. Cl.
| | | |
|---|---|---|
| A61K 31/695 | (2006.01) | |
| A61Q 90/00 | (2009.01) | |
| C07F 7/08 | (2006.01) | |
| A61K 8/04 | (2006.01) | |
| A61K 8/06 | (2006.01) | |
| A61K 8/19 | (2006.01) | |
| A61K 8/25 | (2006.01) | |
| A61K 8/33 | (2006.01) | |
| A61K 8/37 | (2006.01) | |
| C08G 77/46 | (2006.01) | |
| A61K 8/894 | (2006.01) | |
| A61Q 17/04 | (2006.01) | |
| A61Q 19/00 | (2006.01) | |
| A61Q 1/00 | (2006.01) | |
| A61Q 1/02 | (2006.01) | |
| C08G 77/48 | (2006.01) | |

(52) U.S. Cl.
CPC ............... *C08G 77/46* (2013.01); *A61K 8/894* (2013.01); *A61K 8/06* (2013.01); *A61Q 17/04* (2013.01); *A61Q 19/00* (2013.01); *A61Q 1/00* (2013.01); *A61Q 1/02* (2013.01); *A61Q 19/001* (2013.01); *C08G 77/48* (2013.01)
USPC ....................................................... 556/432

(58) Field of Classification Search
CPC ................... A61K 8/894; C08G 77/46
USPC .............. 556/432, 440, 434, 444, 445, 438; 424/70.12; 514/63; 549/214
See application file for complete search history.

(56) References Cited

U.S. PATENT DOCUMENTS

| | | | |
|---|---|---|---|
| 4,431,789 | A | 2/1984 | Okazaki et al. |
| 6,576,623 | B1 | 6/2003 | Nakanishi et al. |
| 2002/0131947 | A1 | 9/2002 | Nakanishi |
| 2005/0008600 | A1 | 1/2005 | Nakanishi et al. |
| 2005/0250904 | A1 | 11/2005 | Okawa et al. |
| 2009/0252774 | A1 | 10/2009 | Kamei et al. |
| 2010/0004201 | A1 | 1/2010 | Matsuo et al. |

FOREIGN PATENT DOCUMENTS

| | | | |
|---|---|---|---|
| JP | B2-04-015762 | 3/1992 | |
| JP | B2-04-020407 | 4/1992 | |
| JP | B2-05-012979 | 2/1993 | |
| JP | B2-05-013126 | 2/1993 | |
| JP | B2-06-062385 | 8/1994 | |
| JP | A-2004-156004 | 6/2004 | |
| JP | 2005-154736 | * 6/2005 | |
| JP | A-2005-154736 | 6/2005 | |
| JP | B2-3724988 | 12/2005 | |
| JP | 2008-218472 | * 8/2006 | ............. B01F 17/52 |
| JP | A-2006-218472 | 8/2006 | |
| JP | B2-3976226 | 9/2007 | |
| JP | A-2009-263213 | 11/2009 | |

OTHER PUBLICATIONS

European Search Report issued in Application No. 11 00 5704; Dated Dec. 13, 2011.
Japanese Office Action issued in Application No. 2010-180421; Dated Dec. 11, 2012 (With Partial Translation).

\* cited by examiner

*Primary Examiner* — Anoop Singh
*Assistant Examiner* — Anna Falkowitz
(74) *Attorney, Agent, or Firm* — Oliff PLC

(57) ABSTRACT

There is disclosed an organopolysiloxane represented by the following general formula (1).

$$R^1-\underset{\underset{R^1}{|}}{\overset{\overset{R^1}{|}}{Si}}-(O-\underset{\underset{R^1}{|}}{\overset{\overset{R^1}{|}}{Si}})_m-C_3H_6CHCH_2CO-Y-OCCH_2CHC_3H_6- \\ \phantom{R^1-Si-O-Si}\underset{COOM}{|} \phantom{-Y-O} \underset{COOM}{|} \\ \phantom{xxxxxxxxxxxxxxxxxxxxxxxxxxxxxxxxx}-(\underset{\underset{R^1}{|}}{\overset{\overset{R^1}{|}}{Si}}-O)_m-\underset{\underset{R^1}{|}}{\overset{\overset{R^1}{|}}{Si}}-R^1 \tag{1}$$

(each $R^1$ independently represents a group selected from an alkyl group having 1 to 30 carbon atoms, a fluorine-substituted alkyl group having 1 to 30 carbon atoms, an aryl group having 6 to 30 carbon atoms, and an aralkyl group having 6 to 30 carbon atoms; Y represents a polyvalent alcohol compound residue; M represents any of a hydrogen atom, an alkaline metal atom, an ammonium ion, and an alkylammonium ion; and reference character m represents an integer of 0 to 300.) There can be an organopolysiloxane capable of providing a cosmetic having excellent emulsion stability, excellent powder-dispersion stability if powders are contained therein, and excellent skin affinity and cosmetic durability, due to a novel organopolysiloxane having a specific structure containing a nonionic hydrophilic group and an anionic hydrophilic group of a carboxylic acid structure; and a cosmetic containing it.

8 Claims, No Drawings

ORGANOPOLYSILOXANE AND COSMETIC CONTAINING THE SAME

BACKGROUND OF THE INVENTION

1. Field of the Invention

The present invention relates to a polyorgnosiloxane having a specific structure containing a hydrophilic group and to a cosmetic containing it, that is, to a polyorganosiloxane with excellent emulsion stability and powder dispersibility and to a cosmetic containing it.

2. Description of the Related Art

A silicone oil is used as an oil component in many applications because of its harmlessness and so on. It is widely used in a cosmetic as well; especially a low-viscosity silicone oil having viscosity of 100 mm$^2$/second or less is widely used in applications such as, for example, skin care and make-up, because of its excellent spreading properties, freshness, and harmlessness.

In the field of a cosmetic and the like, a silicone oil is generally used as emulsion; in that case, a silicone surfactant is used in many cases. As the silicone surfactant, a polyether-modified silicone having a polyoxyalkylene group in the siloxane's terminal or side chain has been known (see for example, Japanese Patent Publication No. H04-15762, Japanese Patent Publication No. H04-20407, Japanese Patent Publication No. H05-13126, Japanese Patent Publication No. H06-62385, Japanese Patent Publication No. H05-12979). In addition, a polyether-modified silicone whose main chain siloxane moiety is branched, disclosed in Japanese Patent No. 3724988, and an ABA-type copolymer, as shown in the following formula (5) disclosed in Japanese Patent Laid-Open Publication No. 2005-154736, have been known as well.

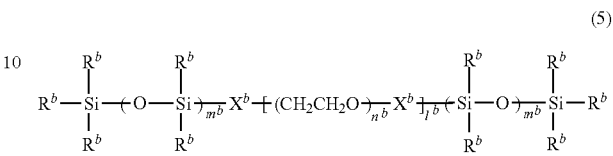

(Wherein, R$^b$ represents a linear or a branched alkylene group having 1 to 12 carbon atoms, or a phenyl group, wherein l$^b$ represents 1 to 5, m$^b$ represents 40 to 90, and n$^b$ represents 10 to 40. X$^b$ represents an arbitrary bonding group, such as a urethane group, a urea group, an amide group, an ester group, and an alkyl ether group.)

As other hydrophilic groups, (poly)glycerine-modified silicones, such as a silicone having a (poly)glycerine group in Japanese Patent Publication No. S62-34039, a silicone having a branched siloxane moiety in Japanese Patent No. 3976226, and an ABA-type copolymer as shown in the following formula (6) in Japanese Patent Laid-Open Publication No. 2006-218472, have been known. These silicones have been known also as a powder-dispersion stabilizer of a powder-containing cosmetic.

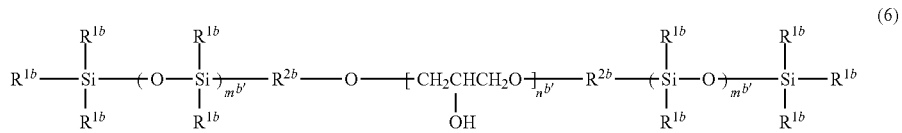

(Wherein, R$^{1b}$ represents a linear or a branched alkyl group having 1 to 12 carbon atoms or a phenyl group, wherein m$^{b'}$ to 120 and n$^{b'}$ represents 1 to 11. R$^{2b}$ is exemplified by an alkylene group having 2 to 11 carbon atoms.)

A silicone surfactant with a different hydrophilic group, bonding position, hydrophilic-hydrophobic (silicone), and so on, is used depending on its use purpose; in particular, an ABA-type copolymer (a silicone-hydrophilic group-silicone type copolymer) has excellent stability for the use in an emulsion cosmetic and a powder-containing cosmetic.

However, the forgoing silicones used as an emulsifying agent and a powder-dispersion stabilizer could not achieve adequate skin affinity and cosmetic durability; thus, a silicone capable of achieving sufficient skin affinity and cosmetic durability, in addition to emulsion stability and powder-dispersion stability, has been desired.

SUMMARY OF THE INVENTION

The present invention has an object to provide: an organopolysiloxane capable of providing a cosmetic having excellent emulsion stability, excellent powder-dispersion stability if powders are contained therein, and excellent skin affinity and cosmetic durability, due to a novel organopolysiloxane having a specific structure containing a nonionic hydrophilic group and an anionic hydrophilic group of a carboxylic acid structure; and a cosmetic containing it.

To solve the problems as mentioned above, the present invention provides an organopolysiloxane represented by the following general formula (1).

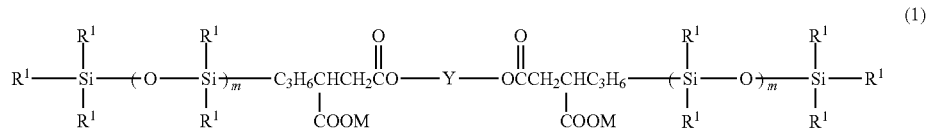

(Wherein, each $R^1$ independently represents a group selected from an alkyl group having 1 to 30 carbon atoms, a fluorine-substituted alkyl group having 1 to 30 carbon atoms, an aryl group having 6 to 30 carbon atoms, and an aralkyl group having 6 to 30 carbon atoms; Y represents a polyvalent alcohol compound residue; M represents any of a hydrogen atom, an alkaline metal atom, an ammonium ion, and an alkylammonium ion; and reference character m represents an integer of 0 to 300.)

Novel organopolysiloxane having a specific structure containing a carboxylic acid shown by the above formula (1) and a cosmetic containing it have excellent emulsion stability, and in addition, excellent powder-dispersion stability if powders are contained therein, and excellent skin affinity and cosmetic durability.

In this case, the polyvalent alcohol compound residue represented by Y is preferably any of a (poly)oxyalkylene residue, a (poly)glycerine residue, and a polyglycerine alkyl ester residue.

The polyvalent alcohol compound residue represented by Y in the above formula (1) is shown by a form that two hydroxy groups are removed from a polyvalent alcohol compound having two or more hydroxy groups per molecule, and is preferably, among them, any of a (poly)oxyalkylene residue, a (poly)glycerine residue, and a polyglycerine alkyl ester residue.

In this case, the organopolysiloxane may be shown by the following general formula (2).

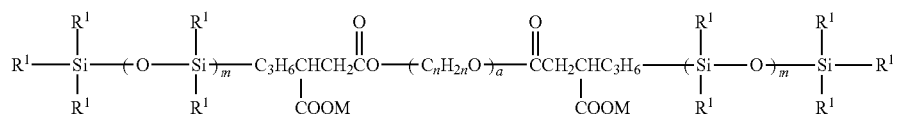

(Wherein, $R^1$, M, and reference character m represent the same meaning as before; reference character n represents an integer of 2 to 6 and reference character a represents integer of 1 to 50.)

As shown above, when Y in the formula (1) is a (poly) oxyalkylene residue, the organopolysiloxane is shown by the foregoing general formula (2).

In this case, the organopolysiloxane may be shown by the following general formula (3).

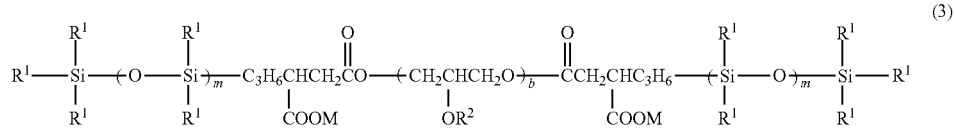

(Wherein, $R^1$, M, and reference character m represent the same meaning as before, and $R^2$ represents a hydrogen atom and a part of $R^2$ may be shown by the following general formula (4). Reference character b represents an integer of 1 to 10.)

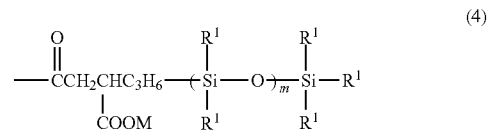

(Wherein, $R^1$, M, and reference character m represent the same meaning as before.)

When Y in the formula (1) is a (poly)glycerine residue as mentioned above, the organopolysiloxane may be shown by the above general formula (3).

In addition, the present invention provides a cosmetic containing the organopolysiloxane in a range between 0.1 and 40% by mass based on the total mass.

The cosmetic containing the organopolysiloxane having a novel specific structure containing a carboxylic acid mentioned above has excellent emulsion stability, excellent powder-dispersion stability if powders are contained therein, and excellent skin affinity and cosmetic durability.

In this case, the foregoing cosmetic may further contain water and may be in a form of an emulsion.

A form of the cosmetic of the present invention is not particularly restricted; but the cosmetic may contain water and may be in a form of an emulsion.

In addition, the cosmetic may further contain at least one or more of a silicone oil, an ester oil, and a glyceride oil, and may be in a form of a non-aqueous emulsion.

As mentioned above, the organopolysiloxane of the present invention is especially effective as an emulsifying agent of a non-aqueous emulsion cosmetic containing a polar solvent usually used in a cosmetic, such as a silicone oil, an ester oil, and a glyceride oil.

In this case, the foregoing cosmetic may further contain powders and may be in a form of a liquid, a paste, or a solid, wherein the powders are dispersed.

A form of the cosmetic of the present invention is not particularly restricted, but may be in a form of a liquid, a paste, or a solid. The organopolysiloxane of the present invention is excellent also in powder dispersibility; and thus, the organopolysiloxane of the present invention may be effectively used in a cosmetic if powders are contained therein. In other words, if the organopolysiloxane of the present invention is blended in a powder-containing cosmetic, a cosmetic having highly dispersed powders may be obtained by powder-treatment effects (water resistance, sebum resistance, and dispersion stability into an oil substance).

The organopolysiloxane of the present invention is excellent in emulsifying properties and powder dispersibility and can form a cosmetic that is excellent in temporal stability, skin-contact properties, and cosmetic durability. In addition, when the organopolysiloxane is blended in a powder-containing cosmetic, a cosmetic having highly dispersed powders can be obtained by powder-treatment effects (water resistance, sebum resistance, and dispersion stability into an oil substance).

DETAILED DESCRIPTION OF THE PREFERRED EMBODIMENTS

Hereinbelow, the present invention will be explained in more detail.

As mentioned above, an organopolysiloxane, having excellent emulsion stability and, in the case that powders are contained in a cosmetic, excellent dispersion stability of powders, and in addition, capable of giving a cosmetic having excellent skin affinity and cosmetic durability, has been desired.

Inventors of the present invention carried out an extensive investigation, and as a result, found that a organopolysiloxane represented by the following general formula (1) has excellent emulsion stability and, in the case that powders are contained therein, excellent dispersion stability, and that a cosmetic blended with the organopolysiloxane has excellent skin affinity and cosmetic durability.

thereof includes an alkyl group such as a methyl group, an ethyl group, a propyl group, a butyl group, a pentyl group, a hexyl group, a heptyl group, an octyl group, a nonyl group, and a decyl group; and a cycloalkyl group such as cyclopentyl group and a cyclohexyl group. The fluorine-substituted alkyl group having 1 to 30 carbon atoms is the alkyl group at least a part of whose hydrogen atoms is displaced with a fluorine atom; and illustrative example thereof includes a trifluoropropyl group and a heptadecafluorodecyl group. Illustrative example of the aryl group having 6 to 30 carbon atoms includes a phenyl group and a tolyl group, and illustrative example of the aralkyl group having 6 to 30 carbon atoms includes a benzyl group and a phenetyl group.

$R^1$ is preferably an alkyl group having 1 to 15 carbon atoms or a phenyl group, or more preferably an alkyl group having 1 to 6 carbon atoms or a phenyl group; or still more preferable $R^1$ is selected from a methyl group and a butyl group. In addition, $R^1$ is comprised of preferably 50% or more of a methyl group, or particularly preferably 70% or more of a methyl group. Best of all, $R^1$ at the molecular chain terminal are preferably a methyl group and a butyl group, wherein the rest of $R^1$ are preferably a methyl group.

Reference character Y in the above general formula (1) is a polyvalent alcohol compound residue which is shown by a form that two hydroxy groups are removed from a polyvalent alcohol compound having at least two or more hydroxy groups per molecule; and Y is not particularly limited as far as Y satisfies this condition. Example of Y is shown by —$CH_2$—$CH_2$—O—$CH_2$—$CH_2$— when diethylene glycol is used as the polyvalent alcohol.

Specific example of the polyvalent alcohol compound residue shown by Y includes a (poly)oxyalkylene residue such as a polyoxyethylene residue, a polyoxypropylene residue, a polyoxybutylene residue, a polyoxypentyl residue, or a block copolymer or a random copolymer of these groups; a (poly) glycerine residue such as a glycerine residue, a diglycerine residue, a triglycerine residue, and a tetraglycerine residue; a (1)

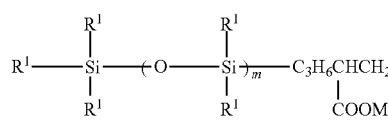 —$C_3H_6CHCH_2CO$— Y —$OCCH_2CHC_3H_6$— 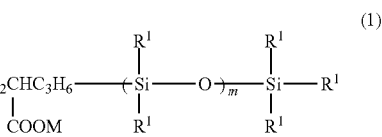
COOM                       COOM (Wherein, each $R^1$ independently represents a group selected from an alkyl group having 1 to 30 carbon atoms, a fluorine-substituted alkyl group having 1 to 30 carbon atoms, an aryl group having 6 to 30 carbon atoms, and an aralkyl group having 6 to 30 carbon atoms; Y represents a polyvalent alcohol compound residue; M represents any of a hydrogen atom, an alkaline metal atom, an ammonium ion, and an alkylammonium ion; and reference character m represents an integer of 0 to 300.)

In the following, the novel organopolysiloxane of the present invention shown by the above formula (1) will be explained in detail.

As to $R^1$ in the above formula (1), the alkyl group having 1 to 30 carbon atoms is a linear, a branched, or a cyclic alkyl group having 1 to 30 carbon atoms; illustrative example polyglycerine alkyl ester residue such as a diglycerine monoalkyl ester residue, a triglycerine monoalkyl ester residue, and a triglycerine dialkyl ester residue; and a pentaerythritol residue. Among them, polyoxyethylene, polyoxypropylene, glycerine, diglycerine, and triglycerine are preferable.

Reference character M in the above general formula (1) represents a hydrogen atom, an alkaline metal atom, an ammonium ion, and an alkylammonium ion; preferably a hydrogen atom and an alkaline metal atom. Reference character m is 0 to 300, or preferably 0 to 150, or more preferably 5 to 100.

In the case that Y in the above formula (1) is a (poly) oxyalkylene residue, the organopolysiloxane of the present invention can be shown by the following general formula (2).

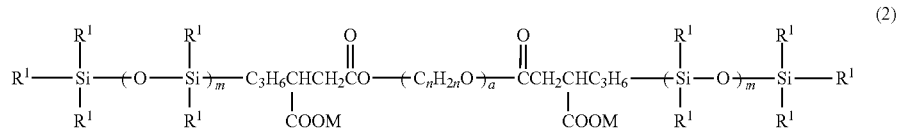
(2)

(Wherein, R¹, M, and reference character m represent the same meaning as before, while reference character n represents an integer of 2 to 6 and reference character a represents an integer of 1 to 50.)

In the case that Y in the above formula (1) is a (poly) glycerine residue, the organopolysiloxane of the present invention can be shown by the following general formula (3).

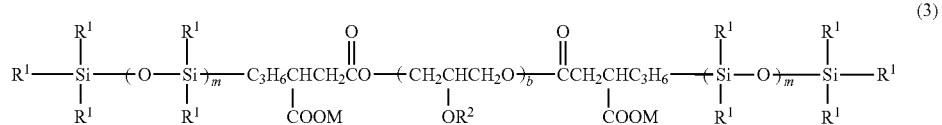
(3)

(Wherein, R¹, M, and reference character m represent the same meaning as before, and R² represents a hydrogen atom wherein a part of R² may be shown by the following general formula (4). Reference character b represents an integer of 1 to 10.)

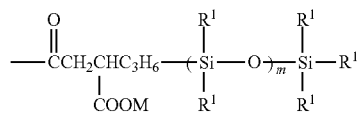
(4)

(Wherein, R¹, M, and reference character m represent the same meaning as before.)

It must be noted here that the polyvalent alcohol compound residue of the present invention may be a group which is shown by a form that two hydroxy groups are removed from a polyvalent alcohol compound having at least two or more hydroxy groups per molecule, as shown above; and a form that a part of hydrogen atoms in other hydroxyl groups is displaced by the above formula (4), namely, as the polyvalent alcohol compound residue, a part of R² in the above general formula (3) is shown by the general formula (4), is included in the present invention.

Because an organopolysiloxane shown by the above formula (1) has excellent skin-contact properties, contains a hydrophilic carboxylic acid group, and is an ABA-type block copolymer comprised of a polysiloxane and a polyvalent alcohol compound residue such as a (poly)oxyalkylene residue, an organopolysiloxane capable of giving a cosmetic that has not only excellent emulsion stability and dispersion stability of powders but also excellent skin affinity and cosmetic durability can be obtained.

The organopolysiolxane of the present invention can be synthesized by the following method.

Step 1:

A polysiloxane having hydrogen(s) on its one end is subjected to an addition reaction with allylsuccinic anhydride shown by the following formula (7) in the presence of a platinum or a rhodium catalyst, so that the acid-anhydride group containing organopolysiloxane can be synthesized.

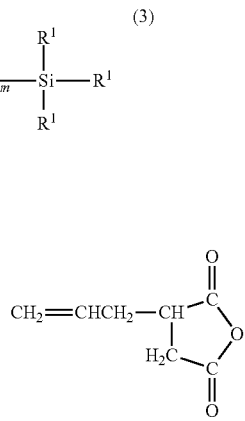
(7)

Step 2:

The organopolysiloxane having the acid anhydride group on its one end synthesized in Step 1 is subjected to a ring-opening reaction with an alcoholic hydroxy group of a polyvalent alcohol compound, so that the organopolysiloxane of the present invention can be obtained. However, as by-products of the ring-opening reaction of the acid anhydride group, an isomer bonded differently and a product resulted by reaction with only one alcoholic hydroxy group of the polyvalent alcohol may also be included in some cases.

The carboxylic acid obtained in Step 2 is reacted with sodium hydroxide, an aqueous ammonia, and so on, so that a compound whose M is an alkaline metal and an ammonium ion can be obtained.

The total reaction ratio of the polysiloxane having hydrogen on its one end to the unsaturated-group containing compound (allylsuccinic anhydride shown by the above formula (7)) in Step 1 is 0.5 to 2.0, or preferably 0.8 to 1.2, as the mole ratio of the SiH group on one end to the unsaturated group.

The addition reaction in Step 1 is preferably carried out in the presence of a platinum or a rhodium catalyst; for example, a chloroplatinate, an alcohol-modified chloroplatinate, and a chloroplatinate-vinyl siloxane complex may be preferably used. Here, an effective amount of the catalyst may be sufficient; for example, the amount as platinum or rhodium is 50 ppm or less, or preferably 20 ppm or less.

The addition reaction may be carried out in an organic solvent as appropriate; illustrative example of the organic solvent includes an aromatic hydrocarbon such as toluene and xylene; an aliphatic or an alicyclic hydrocarbon such as n-pentane, n-hexane, and cyclohexane; a halogen-containing hydrocarbon such as dichloromethane, chloroform, and carbon tetrachloride; an ether such as tetrahydrofurane and dioxane; and a ketone such as acetone and methyl ethyl ketone. Preferably, the reaction is carried out without solvent, or in a hydrocarbon solvent or in an ether solvent.

Conditions of the addition reaction are not particularly restricted; when a solvent is used, the reaction is carried out preferably under reflux of a solvent, if used, for 1 to 10 hours.

The reaction ratio of the organopolysiloxane having an acid anhydride group on its one end to the polyvalent alcohol compound in Step 2 is 0.5 to 1.1, or preferably 0.7 to 1.0, as the mole ratio of the alcoholic hydroxy group to the acid anhydride group.

Examples of the polyvalent alcohol compound used in Step 2 include, for example, (poly)oxyalkylene compound such as ethylene glycol, diethylene glycol, triethylene glycol, polyethylene glycol (molecular weight of 200 to 2000), propylene glycol, dipropylene glycol, polypropylene glycol (molecular weight of 200 to 3000), butylene glycol, dibutylene glycol, polybutylene glycol (molecular weight of 200 to 4000), random copolymer and block copolymer of polyethylenepropylene glycol (molecular weight of 100 to 3000), and random copolymer and block copolymer of polyethylenebutylene glycol (molecular weight of 100 to 4000); (poly) glycerine compound such as glycerine, diglycerine, triglycerine, polyglycerine having molecular weight of 1000 or less, and isomer thereof: polyglycerinealkylester compound such as diglycerinmonooleylester, diglycerinmonostearylester, triglycerinmonooleylester, triglycerindistearylester; and pentaerythritol.

The ring-opening reaction can take place easily even without a catalyst; but an inorganic salt such as potassium acetate and sodium acetate may be used as the catalyst. The reaction may be carried out in a solvent as appropriate; illustrative example of the organic solvent includes an aromatic hydrocarbon such as toluene and xylene; an aliphatic or an alicyclic hydrocarbon such as n-pentane, n-hexane, and cyclohexane; a halogen-containing hydrocarbon such as dichloromethane, chloroform, and carbon tetrachloride; an ether such as tetrahydrofurane and dioxane; and a ketone such as acetone and methyl ethyl ketone. Preferably, the reaction is carried out without solvent, or in a hydrocarbon solvent or in an ether solvent.

The organopolysiloxane of the present invention is preferably used in an external cosmetic for skin and hair. In particular, the organopolysiloxane is preferably used as an emulsifying agent in a cosmetic that contains a silicone usually used in a cosmetic and a polar solvent such as water, a glycol, an ester oil, and a glyceride oil, and as a dispersing agent for a powder-containing cosmetic. Amount of the organopolysiloxane blended therein is preferably 0.1 to 40% by mass, or more preferably 0.5 to 20% by mass, based on the total cosmetic mass. In the case of a powder-containing cosmetic, amount of the organopolysiloxane is preferably 1 to 40 parts by mass, or in particular 1 to 20 parts by mass, relative to 100 parts by mass of the powders.

Into the cosmetic of the present invention can be blended one, or two or more, of an oil material depending on its purpose. An oil material in any form of a solid, a semi-solid, and a liquid can be used as far as it is used in a usually used cosmetic; illustrative example of the oil material includes a natural plant or animal oil or a semi-synthetic oil, a hydrocarbon oil, a higher alcohol, an ester oil, a usually used silicone oil, and a fluorinated oil material.

Examples of the natural plant or animal oils and semi-synthetic oils include avocado oil, linseed oil, almond oil, Ibota wax, perilla oil, olive oil, cacao butter, kapok wax, kaya oil, carnauba wax, cod-liver oil, candelilla wax, purified candelilla wax, beef tallow, neat's-foot oil, beef bone fat, hydrogenated beed tallow, apricot kernel oil, spermaceti wax, hydrogenated oil, wheat germ oil, sesame oil, rice germ oil, rice bran oil, sugarcane wax, sasanqua oil, safflower oil, shea butter, Chinese tung oil, cinnamon oil, jojoba wax, squalane, squalene, shellac wax, turtle oil, soybean oil, tea seed oil, camellia oil, evening primrose oil, corn oil, lard, rapeseed oil, Japanese tung oil, rice bran wax, germ oil, horse fat, persic oil, plam oil, plam kernel oil, castor oil, hydrogenated castor oil, castor oil fatty acid methylester, sunflower oil, grape oil, bayberry wax, jojoba oil, macadamia nut oil, beeswax, mink oil, meadowfoam oil, cottonseed oil, cotton wax, Japanese wax, Japanese wax kenel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, lanolin acetate alcohol, isopropyl lanolate, POE lanolin alchol ether, POE lanolin alchol acetate, polyethylene glyol lanolate, POE hydrogenated lanolin alchol ether, and egg yolk oil, wherein POE represents polyoxyethylene.

Examples of the hydrocarbon oil include linear, branched, and further volatile hydrocarbon oil. Especially, ozokerite, α-olefin oligomer, light isoparaffin, isododecane, isohexadeane, light liquid isoparaffin, squalane, synthetic squalane, plant-origin squalane, squalene, ceresin, paraffin, paraffin wax, polyethylene wax, polyethylene/polypropylene wax, (ethylene/propylene/styrene) copolymer, (butylene/propylene/styrene) copolymer, liquid paraffin, liquid isoparaffin, pristane, polyisobutylene, hydrogenated polyisobutene, microcrystalline wax, and vaseline.

Examples of higher fatty acids include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxysteatic acid are exemplified.

Examples of the higher alchol include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alchol, 2-decyltetradecinol, cholesterol, phytosterol, POE chlolesterol ether, monostearyl glycerin ether (batyl alcohol), and monooleyl glyceryl ether (ceralyl alcohol).

Examples of the ester oil include diisobutyl adipate, 2-hexyl decyl adipate, di-2-heptylundecyl adipate, N-alkyl glycol monoisostearate, isocetyl isostearate, trimethylolpropan triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentylglycol dioctanoate, neopentyl glycol dicapriate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isononyl isononanate, isotridecyl isononanate, isopropyl palmitate, 2-ethyl-hexyl palminate, 2-hexyldecyl palminate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, lauroyl sarcosine isopropylester, diisostearyl malate.

Examples of glyceride oils include acetoglyceryl, glyceryl triisooctanoate, glyceryl triisostearate, glyceryl triisopalmitate, glyceryl tribehenate, glyceryl monostearate, glyceryl di-2-heptyl undecanate, glyceryl trimyristynate, diglyceryl myristyl isostearate.

Examples of the silicone oil include linear or branched organopolysiloxanes having low to high viscosities such as dimethylpolysiloxane, tristrimethylsiloxymethylsilane, caprylyl methicone, phenyltrimethicone, tetrakistrimethylsiloxysilane, methylphenylpolysiloxane, methylhexylpolysiloxane, methylhydrogenpolysiloxane, and copolymers of dimethyl siloxane and methylphenylsiloxane; cyclic organopolysiloxanes such as octamethylcyclotetrasiloxane, decamethylcyclopentasiloxane, dodecamethylcyclohexasiloxane, tetramethyl-tetrahydrogencyclotetrasiloxane, and tetramethyl-tetraphenyl cyclotetrasiloxane and tetramethyltetraphenylcyclotetrasiloxane; amino-modified organopolysiloxanes, pyrrolidonyl-modified organopolysiloxanes, pyrrolidonyl/carboxy-modified organopolysiloxanes; silicone rubbers such as gummy dimethylpolysiloxanes having high polymerization degrees, gummy amino-modified organopolysiloxanes, and gummy dimethylsiloxane/methylphenylsiloxane copolymers and silicone rubber or gum in cyclic organopolysiloxane solution; trimethylsiloxysilicate, and trimethylsiloxysilicate in cyclic siloxane solution, higher alkoxy-modified silicones such as stearoxysilicone, higher fatty acid-modified silicones, alkyl-modified silicones, long chain alkyl-modified silicones, aminoacid-modified silicones, fluorinated silicones, silicone resins and solutions of silicone resin.

Examples of the fluorinated oil include perfluoropolyether, perfluorodecaline, and perfluorooctane. The content amout of these oil, which is different by system, preferably 1 to 98 mass % relative to the total amount of the cosmetics.

In the cosmetics of the present invention, water may be added accoding to the object thereof. The content amount, which is different by system, is preferably 1 to 95 mass % relative to the total amount of the cosmetics.

In the cosmetics of the present invention, one or more kinds of $C_{2-5}$ lower alcohols and $C_{2-10}$ polyalcohols may be added accoding to the object thereof.

Examples of the alcohol includes lower alcohols such as ethanol, and isopropanol; sugar alcohols such as sorbitol, and maltose; sterols such as cholesterol, sitosterol, phytosterol, and lanosterol; and polyalcohols such as butylene glycol, propylene glycol, dibutylene glycol, and pentylene glycol. A content of the alcholes can be varied from 0.1 to 98 mass % relative to a total weight of the cosmetic.

Water-soluble or water-swellable polymer may be added to the cosmetics of the present invention as appropriate according to the object thereof. Among them, one or two or more kinds of water-soluble gum selected from plant-derived polymers, bacteria-derived polymers, animal-derived polymers, starch-derived polymers, cellulose polymers, alginic acid-derived polymers, polyoxyethylene/polyoxypropylene copolymers, acrylic polymers, inorganic water-soluble agents are preferably used.

Examples thereof are plant-derived polymers such as gum Arabic, tragacanth gum, galactan, carob gum, guar gum, karaya gum, carrageenan, pectin, agar-agar, quice seed (i.e., marmelo), starch (rice, corn, potato, wheat etc.), algae colloid, trant gum and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxylmethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol ester alginate; vinyl polymers such as polyvinyl methylether, and carboxyvinyl polymer; polyoxyethylene polymer; polyoxyethylene/polyoxypropylene copolymers; acrylic polymers such as sodium poly acrylate, polyethyl acrylate, polyacrylamide, and acryloyl dimethyl taurate copolymer; polyethyleneimine; cationic polymers; and inorganic thickening agents such as, bentonite, aluminum magnesium silicate, montmorillonite, videlite, nontronite, saponite, hectorite, and silicic anhydride. An amount of the water-solubule or water-swellabule polymer in the cosmetic ranges preferably from 0.1 to 25 mass % relative to a total amount of the cosmetic.

In the present mention, one kind or two or more kind of powders may be used. Any powder which is commonly used in cosmetics may be used, regardless of the shape such as spherical, acicular, and plate-like; particle size such as fume size, fine particles and pigment grade; and particle structure such as porous and non-porous. Examples of the powder include inorganic powder, organic powder, metal salt powder of surfactant, colored pigments, pearl pigments, metallic powder pigments, tar colors, and natural colors.

Examples of the inorganic powder include powder of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, and silica.

Examples of the organic powder include powder of polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, nylon powder, Nilon-12 powder, Nylon-6 powder, silicone powder, styrene/acrylic acid copolymer, divinylbenzen/styrene copolymer, vinyl resin, urea resin, phenol resin, fluorinated resin, silicone resin, acrylate resin, melamine, epoxy resin, polycarbonate resin, microcrystalline fiber powder, starch powder, and lauroyl lysine powder.

Examples of the powder of metal salt of surfactant (metal soaps) include powder of zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of colored pigments include powder of inorganic red pigments such as pigments composed of iron oxide, iron hydroxide, and iron titanate, inorganic brown pigments such as γ-iron oxide, inorganic yellow pigments such as iron oxide yellow, and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar colors, lakes of natural colors, and composite powders of these powder with a synthetic resin.

Examples of the pearl pigments include powder of titanium oxide-coated mica, titanium oxide-coated mica, bismuth oxychloride, titanium oxide-coated bismuthoxychloride, titanium oxide-coated talc, fish scales, and titanium oxide-coated colored mica; and metallic powder pigments such as aluminum powder, copper powder and stainless powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207; and natural colors such as carminic acid, laccaic acid, carthamin, brazilin, and crocin.

As the powder, the aforementioned powder as it is and composite thereof can be used. The powder may be treated with a general oil, silicone oil, fluorine compound, or surfactant. A linear or branced organopolysloxane having a hydrolysable silyl group or SiH bond, a linear or brancked organopolysiloxane having a long alkyl chain and hydrolysable silyl group or SiH bond, a linear or branched organopolysiloxane having a polyocxyalkylene moiety and hydroysable silyl group or SiH bond, an acryl silicone copolymer hagving a hydrolysable silyl group or SiR bond may be used. Two ore more of the treatment agents may be employed. The powder and/or colorants is incorporated in the cosmetic in such an amount that it does not adversely affect the present invention.

The content amount of the powder is preferably 0.1 to 99 mass % relative to total amount of the cosmetics. Especially, in the case of powder-solid cosmetics, the content of the powder is preferably 80 to 99 mass % relative to total amout of the cosmetics.

In the cosmetic of the present invention, one or more kinds of surfactant can be used. Examples of the surfactant include an anionic, cationic, nonionic or amphoteric surfactant. The surfactant is not limited to them. Any surfactant which is commonly used in cosmetics may be used.

Examples of the anionic surfactant include fatty acid soaps, such as sodium stearate and triethanolamine palmitate, alkylether carboxylic acid and salts thereof, salts of condensates of amino acids with fatty acids, alkanesulfonate, alkenesulfonates, sulfonates of fatty acid esters, sulfonates of fatty acid amide, sulfonate of the formalin condensates, alkyl sulfate ester salts, secondary higher alchol sulfate ester salts, alkyl/allyl ether sulfate ester salts, fatty acid ester sulfate ester salts, fatty acid alkylolamide sulfate ester salts, and Turkey Red oil sulfate ester salts, alkyl phosphate salts, ether phosphate salts, alkylallylether phosphate salts, amide phosphate salts, N-acyl lactate, N-acyl sarcosinate and N-acylamino surfactantants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyetylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, liner or branched polyoxyalkylene-modified organopolysiloxane, linear or branced polyoxyalkylene/alkyl-comodified organopolysiloxane, polyglycerin modified organopolysiloxane, polyglycerin/alkyl-comodified organopolysiloxane, alkanolamide, sugar ethers, and sugar amides.

Illustrative example of the ampholytic surfactant includes a betaine, a phosphatidyl choline, an amino carboxylic acid salt, an imidazoline derivative, and an amide-amine type. Among these surfactants, a linear or a branched organopolysiloxane having a polyoxyalkylene chain or a polyglycerine chain in its molecule, or a linear or a branched organopolysiloxane further containing a long chain alkyl group having 6 to 20 carbon atoms is preferable.

In addition, it is preferable that, in these surfactants, content amount of a hydrophilic polyoxyalkylene group or a polyglycerine residue occupy 10 to 70% by mass in a molecule; and the blending amount thereof is preferably 0.1 to 20% by mass, or in particular 0.2 to 10% by mass, based on the total cosmetic mass.

The cosmetic of the present invention may contain a silicone resin selected from an acryl silicone resin and a reticular silicone resin. The acryl silicone resin is a graft or a block copolymer of an acryl and a silicone. In addition, an acryl silicone resin containing in its molecular structure at least one kind selected from the group consisting of a pyrrolidinyl group, a long chain alkyl group, a polyoxyalkylene group, a fluoroalkyl group, and an anionic group such as a carboxyl group may be used.

The reticular silicone resin may be selected from a resin comprised of a $R^{1s}_3SiO_{0.5}$ unit and a $SiO_2$ unit; a resin comprised of a $R^{1s}_3SiO_{0.5}$ unit, a $R^{1s}_2SiO$ unit, and a $SiO_2$ unit; a resin comprised of a $R^{1s}_3SiO_{0.5}$ unit and a $R^{1s}SiO_{1.5}$ unit; a resin comprised of a $R^{1s}_3SiO_{0.5}$ unit, a $R^{1s}_2SiO$ unit, and a $R^{1s}SiO_{1.5}$ unit; and a resin comprised of a $R^{1s}_3SiO_{0.5}$ unit, a $R^{1s}_2SiO$ unit, a $R^{1s}SiO_{1.5}$ unit, and a $SiO_2$ unit. Here, $R^{1s}$ represents a hydrocarbon group. In addition, a reticular silicone resin containing in its molecular structure at least one kind selected from the group consisting of a pyrrolidinyl group, a long chain alkyl group, a polyoxyalkylene group, a fluoroalkyl group, and an amino group may also be used. Blending amount of the silicone resin if used is preferably 0.1 to 20% by mass, or more preferably 1 to 10% by mass, based on the total cosmetic mass.

Alternatively, in the cosmetic of the present invention, a composition comprised of an oil material that is in a liquid form at room temperature and one, or two or more, of a crosslinked organopolysiloxane, depending on its purpose, may be used. It is preferable that the crosslinked organopolysiloxane be swollen by containing the liquid oil with the amount more than the weight of itself relative to the liquid oil, Illustrative example of the liquid oil includes the silicone oil, a hydrocarbon oil, an ester oil, a natural plant or animal oil, a semi-synthetic oil, and a fluorinated oil, as mentioned above, which are liquid state; and an example thereof includes a low-viscosity silicone oil having viscosity of 0.65 to 100.0 $mm^2$/second (at 25° C.); a hydrocarbon oil such as a liquid paraffin, squalane, isododecane, and isohexadecane; a glyceride oil such as trioctanoin; an ester oil such as isotridecyl isononanate, an N-acylglutamate ester, and a lauroyl sarcocinate ester; and a natural plant or animal oil such as a macademia nut oil. A crosslinking agent used in this crosslinkable organopolysiloxane is preferably the one that has two or more reactive vinyl moieties per molecule and can react with a hydrogen atom directly bonded to a silicon atom thereby forming a crosslinked structure. Illustrative example of the crosslinking agent having two or more reactive vinyl moieties per molecule includes an organopolysiloxane having two or more vinyl groups per molecule, a polyoxyalkylene having two or more allyl groups per molecule, a polyglycerine having two or more allyl groups per molecule, and an α, ω-alkenyldiene. Alternatively, a crosslinking agent having at least one kind selected from the group consisting of a polyoxyalkylene group, a polyglycerine residue, a long chain alkyl group, an alkenyl group, an aryl group, and a fluoroalkyl group may be used. When a composition comprised of a crosslinkable organopolysiloxane and an oil material that is in a liquid form at room temperature is used, the blending amount thereof is preferably 0.1 to 80% by mass, or more preferably 1 to 50% by mass, based on the total cosmetic mass.

The cosmetic of the present invention may contain a silicone-modified olefin wax obtained by an addition reaction of an olefin wax containing an unsaturated group—obtained by a reaction between a diene and, depending on the purpose, one, or two or more, of α-olefins—with an organohydrogen polysiloxane having one or more SiH bonds per molecule. Preferable example of the α-olefin includes an α-olefin having 2 to 12 carbon atoms such as ethylene, propylene, 1-butene, 1-hexene, and 4-methyl-1-pentene; and as the dienes, butadiene, isoprene, 1,4-hexadiene, vinyl norbornene, ethylidene norbornene, dicyclopentadiene, and the like are preferable. As the SiH-bond containing organohydrogen polysiloxane, those having a structure of a linear, a siloxane branched type, or the like can be used.

The cosmetic of the present invention may be added with a component generally used in a usual cosmetic in a range not to adversely affect the effects of the present invention; illustrative example thereof includes an oil-soluble gelling agent, an organic-modified clay mineral, an antiperspirant, a UV (ultraviolet)-absorber, a UV absorbing-scattering agent, a moisturizer, a preservative, an antibacterial agent, a fragrance, a salt, an antioxidant, a pH-controller, a chelating agent, an algefacient, an anti-inflammatory agent, a skin care component (a skin-lightening agent, a cell activator, a rough-skin improver, a blood circulation promoter, a skin astringent agent, an antiseborrheic agent, and so on), a vitamin, an amino acid, a nucleic acid, a hormone, a clathrate compound, and a hair-immobilizing agent.

Examples of the oil-soluble gelling agent include metal soaps, such as aluminum stearate, magnesium stearate and zinc myristate; amino acid derivatives, such as N-lauroyl-L-glutamic acid and α, γ-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; fructooligo fatty acid esters such as fructooligo stearic acid ester and fructooligo 2-ethylhexylic ester; benzylidene derivatives of sorbitol, such as monobenzylidene sorbitol and dibenzylidene sorbitol: and an organic-modified clay mineral, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesguichloro-hydrate, zirconium hydroxychloride, aluminum zirconium hydroxychloride, and aluminum zirconium glycine complex.

Examples of the UV absorber include UV absorber of benzoic acid type such as p-aminobenzoic acid; those of anthranilic acid type such as methyl anthranilate; those of salicyclic acid type such as methyl salicylate, octyl salicylate, and trimethylcyclohexyl salicylate; those of cinnamic acid type such as oactyl p-methoxycinnamate; those of benzophenone type, such as 2,4-dihydroxybenzophenone; those of urocanic acid type, such as ethyl urocanate; those of dibenzoyl-methane type such as 4-t-butyl-4'-methoxydibenzoylmethane; phenylbenzimidazol sulfonic acid and triazine derivatives. Examples of the UV absorbing-scattering agents include fine powder of titanium oxide, fine powder of iron-containing titanium oxide, firer powder of zinc oxide, fine powder of cerium oxide, a complex of these powders and powders which abosorb-scatter ultraviolet. Dispersion of these UV absorbing-scattering agents in an oil can be used too.

Examples of moisturizer include glycerin, sorbitol, propylene glycol, dipropylene glycol, 1,3-butylene glycol, pentylene glycol, glucose, xylitol, maltitol, popyethylene glycol, hyaluronic acid, chondroitin sulfuric acid, pyrrolidone carboxylate, polyoxyethylene methylglycoside, and polyoxypropylene methylglycoside, egg-yolk lecithin, soy beans lecithin.

Examples of the preservative include paraoxybenzoate alkyl ester, benzoic acid, aodium benzoate, sorbic acid, potassium sorbate, and phenoxyethanol may be used. For the antibacterial agents, benzoic acid, salicylic acid, carbolic acid, sorbic acid, paraoxybenzoate alkyl ester, parachlorometha-cresol, hexachlorophene, benzalkonium chloride, chlorohexydine chloride, trichlorocarbanilide, photopigment and phenoxyethanol.

Examples of the salts include inorganic salts, organic acid salts, salts of amine and salts of amino acids.

Examples of the inorganic salts include sodium, potassium, magnesium, calcium, aluminum, zirconium, or zinc salt of inorganic acid such as hydrochloric acid, sulfuric acid, carbonate acid, and nitric acid. Examples of the salts of organic acid include salts of organic acid such as acetic acid, dehydroacetic acid, citric acid, malic acid, succinic acid, ascorbic acid, and stearic acid. Examples of the salts of amine or amino acid include salt of amine such as triethanol amine and salt of amino acid such as glutamic acid. Other examples are salt of hyaluronic acid, chondroitin sulfate, aluminum/zirconium/glycine chelate, and salts produced by acid-alkaline neutralization reaction in the cosmetic.

Examples of the antioxidants include tocopherol, p-t-butylphenol, butylhydroxyanisole, dibutylhydroxytoluene and phytic acid; examples of the pH regulators include lactic acid, citric acid, glycolic acid, succinic acid, tartatic acid, dl-malic acid, potassium carbonate, sodium hydrogen carbonate and ammonium hydrogen carbonate; examples of the chelating agents include alanine, edetate sodium, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents, such as placenta extract, arbutin, glutathione and Yukinoshita extract; cell activators, such as royal fully, photosensitizers, cholesterol derivatives and calt blood extract; rough and dry skin improvers; blood circulation improvers, such as nonylic acid vanillyl amide, benzyl nicotinate, β-butoxyethyl niconinate, capsaicin, zingerone, cantharis tincture, ichtammol, caffeine, tannic acid, α-borneol, tocopherol nicotinate, inositol hexanicotinate, cyclandelate, cinnarizine, tolazoline, actyl choline, verapamil, cepharanthin and gamma-oryzanol; skin astringents, such as zinc oxide and tannic acid; and anti-seborrheic agents, such as sulfur and thiathol.

Examples of the vitamins include vitamin A, such as vitamin A oil, retinol, retinyl acetate, and retinyl palmitate; vitamin B, including vitamin B2 such as riboflavin, riboflavin butyrate and flavin adenine nucleotide, vitamin B6 such as pyridoxine hydrochloride, pyridoxine dioctanoate and pyridoxine tripalmitate, vitamin B12 and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α- tocopheryl succinate; vitamin H; vitamin P; nicotinic acids, such as nicotinic acid, benzyl nicotinate and nicotinic acid amide; pantothenic acids, such as calcium pantothenate, O-pantothenyl alcohol, pantothenyl ethyl ether and acetylpantothenyl ethyl ether; and biotin.

Examples of the amino acids include glycine, valine, leucine, isoleucine, serine, threonine, phenylaranine, arginine, lysine, aspartic acid, glutamic acid, cystine, cysteine, methionine, and tryptophan; examples of the nucleic acids include deoxyribonucleric acid; and examples of the hormones include estradiol and ethenyl estradiol.

Examples of the polymers for hair setting include amphoteric, anionic, cationic, and nonionic polymers, such as polymers of polyvinyl pyrrolicone type such as polyviniyl pyrrolidone, vinyl pyrrolidone/vinyl acetate copolymers; acidic polymers of vinyl ether type such as methyl vinyl ether/maleic acid anhydride alkyl half ester copolymer; polymers of acidic poly vinyl acetate type such as vinyl acetate/crotonic acid copolymer; acidic acrylic polymers such as (meth) acrylic acid/alkyl (meth)acrylate copolymer, (meth)acrylic acid/alkyl (meth)acrylate/alkyl acrylic amide copolymer, and amphoteric acrylic polymer such as N-meth-acryloylethyl-N, N-dimethylammonium α-N-methylcarboxybetaine/alkyl (meth)acrylate copolymer, hydroxypropyl(meth)acrylate/butylaminoethyl methacrylate/octyl amide of acrylic acid copolymer. Use is also made of naturally occurring polymers such as cellulose or derivatives thereof, keratin, collagen and derivatives thereof.

The cosmetic can be in various forms, for example, aqueous, oily, oil-in-water type emulsion, water-in-oil type emulsion, non-aqueous emulsion, multi-emulsion such as W/O/W or O/W/O emulsion, paste form, and solid state.

The cosmetic may be used in the various product forms. Examples of the cosmetic include skin care cosmetic, such as face lotion, milky lotion, cream, face cleansing cream, facial mask, oil liquid, massage materials, essence, essence oil, hand cream, lip cream, creaseproof material; makeup cosmetic, such as makeup base, concealer, face powder, powder foundation, liquid foundation, cream foundation, oil-based foundation, teak color, eye shadow, mascara, eyeliner, eyeblow, and lipstick; and hairdressing cosmetic, such as shampoo, rinse, treatment, and setting agent; UV protective cosmetics, such as sunscreen oil, sunscreen milky lotion and sunscreem cream; cleansing agent; air refresher; and antiperspirant.

EXAMPLES

In the following, the present invention will be explained by referring to Examples; but the present invention is not limited to them.

Example 1

Into a reactor were charged 241 parts by mass of polysiloxane having hydrogen on its one end, shown by the following formula (8), 14.7 parts by mass of allylsuccinic anhydride, and 100 parts by mass of toluene; and after 0.1 part by mass of toluene solution containing 0.5% by mass of chloroplatinate was added, the reaction was carried out under reflux for two hours. The obtained reaction mixture was heated under reduced pressure to distill out the solvent to obtain an acid-anhydride group containing organopolysiloxane shown by the following formula (9).

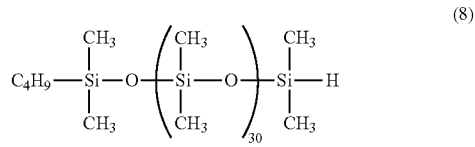

To 255 parts by mass of the foregoing acid-anhydride group containing organopolysiloxane were added 20.7 parts by mass of polyethylene glycol (HO(C₂H₄O)₉H) and 0.01 part by mass of sodium acetate; and then the reaction was carried out at 80° C. for 5 hours. The reaction mixture was subjected to distillation under reduced pressure to obtain a carboxyl group-containing organopolysiloxane shown by the following formula (10).

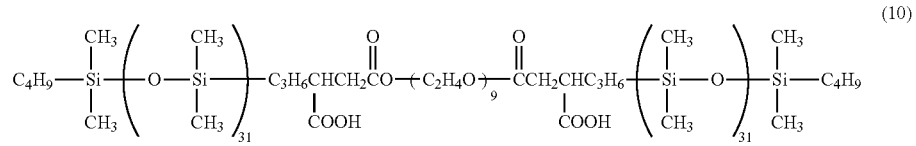

Example 2

Into a reactor were charged 463 parts by mass of polysiloxane having hydrogen on its one end, shown by the following formula (11), 14.7 parts by mass of allylsuccinic anhydride, and 200 parts by mass of toluene; and after 0.1 part by mass of toluene solution containing 0.5% by mass of chloroplatinate was added, the reaction was carried out under reflux for two hours. The obtained reaction mixture was heated under reduced pressure to distill out the solvent to obtain an acid-anhydride containing organopolysiloxane shown by the following formula (12).

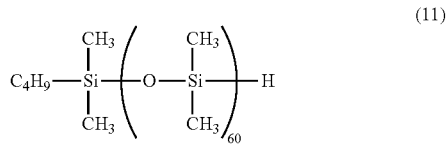

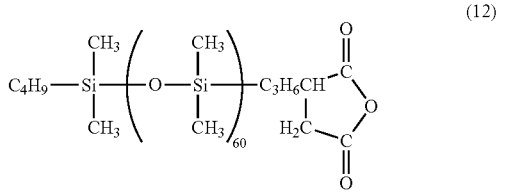

(12)

To 464 parts by mass of the foregoing acid-anhydride group containing organopolysiloxane were added 7.6 parts by mass of diglycerine and 0.01 part by mass of sodium acetate; and then the reaction was carried out at 80° C. for 5 hours. The reaction mixture was subjected to distillation under reduced pressure to obtain a carboxyl group-containing organopolysiloxane shown by the following formula (13).

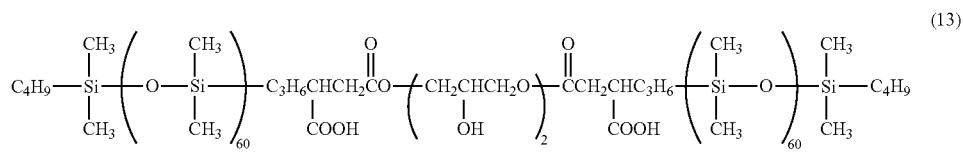

(13)

Example 3

To 232 parts by mass of the acid-anhydride group containing, modified organopolysiloxane (12) obtained in Example 2 were added 38.7 parts by mass of $HO(C_2H_4O)_{15}(C_3H_6O)_{15}H$ and 0.01 part by mass of sodium acetate; and then the reaction was carried out at 80° C. for 5 hours. The reaction mixture was subjected to distillation under reduced pressure to obtain a carboxyl group-containing organopolysiloxane shown by the following formula (14).

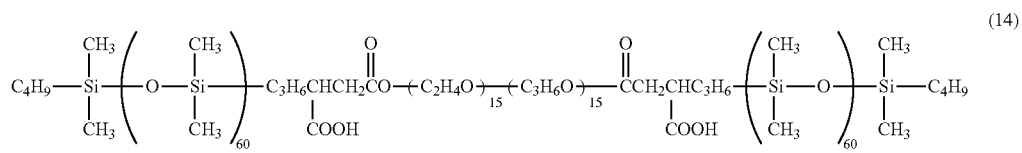

(14)

Example 4

To 255 parts by mass of the acid-anhydride group containing, modified organopolysiloxane (9) obtained in Example 1 were added 21.6 parts by mass of diglycerine monostearate and 0.01 part by mass of sodium acetate; and then the reaction was carried out at 80° C. for 8 hours. The reaction mixture was subjected to distillation under reduced pressure to obtain the carboxyl group-containing organopolysiloxane shown by the following formula (15).

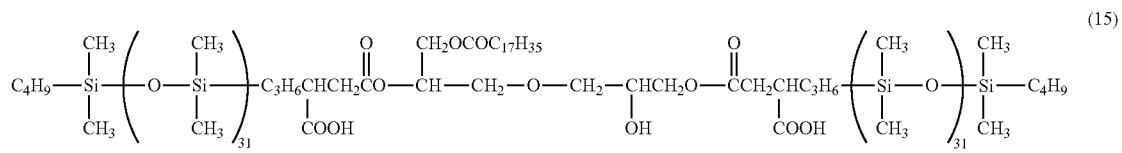

(15)

Example 5

Into a reactor were charged 229 parts by mass of polysiloxane having hydrogen on its one end, shown by the following formula (16), 1.5 parts by mass of allylsuccinic anhydride, and 100 parts by mass of toluene; and after 0.1 part by mass of toluene solution containing 0.5% by mass of chloroplatinate was added, the reaction was carried out under reflux for two hours. The obtained reaction mixture was heated under reduced pressure to distill out the solvent to obtain a acid-anhydride group containing organopolysiloxane shown by the following formula (17).

Example 6

Into a reactor were charged 583 parts by mass of polysiloxane having hydrogen on its one end, shown by the following formula (19), 14.7 parts by mass of allylsuccinic anhydride, and 200 parts by mass of toluene; and after 0.1 part by mass of toluene solution containing 0.5% by mass of chloroplatinate was added, the reaction was carried out under reflux for two hours. The obtained reaction mixture was heated under reduced pressure to distill out the solvent to obtain a acid-anhydride group containing organopolysiloxane shown by the following formula (20).

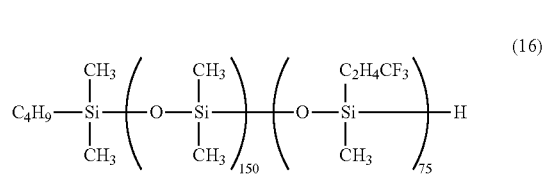

(16)

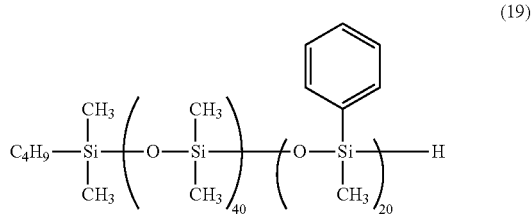

(19)

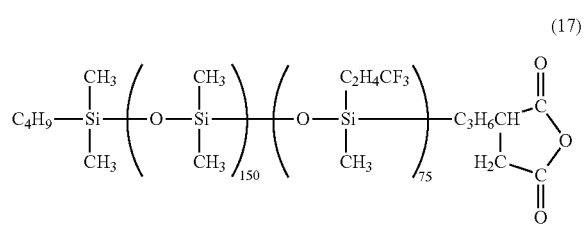

(17)

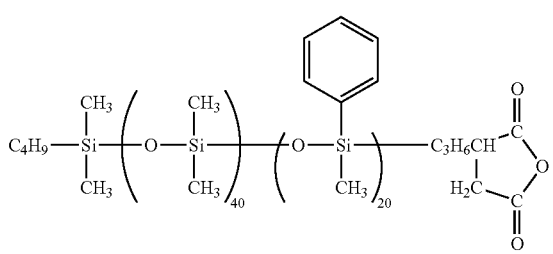

(20)

To 230 parts by mass of the foregoing acid-anhydride group containing organopolysiloxane were added 1.2 parts by mass of triglycerine and 0.01 part by mass of sodium acetate; and then the reaction was carried out at 80° C. for 5 hours. The reaction mixture was subjected to distillation under reduced pressure to obtain a carboxyl group-containing organopolysiloxane shown by the following formula (18).

To 179 parts by mass of the foregoing acid-anhydride group containing organopolysiloxane were added 2.2 parts by mass of triglycerine and 0.01 part by mass of sodium acetate; and then the reaction was carried out at 80° C. for 5 hours. The reaction mixture was subjected to distillation under reduced pressure to obtain a carboxyl-containing organopolysiloxane shown by the following formula (21).

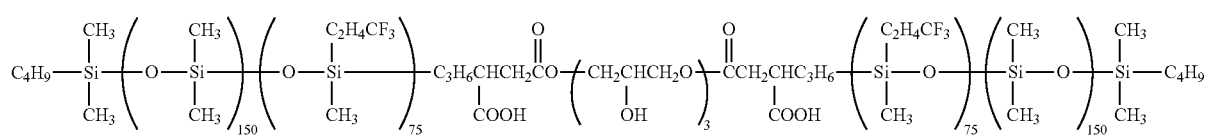

(18)

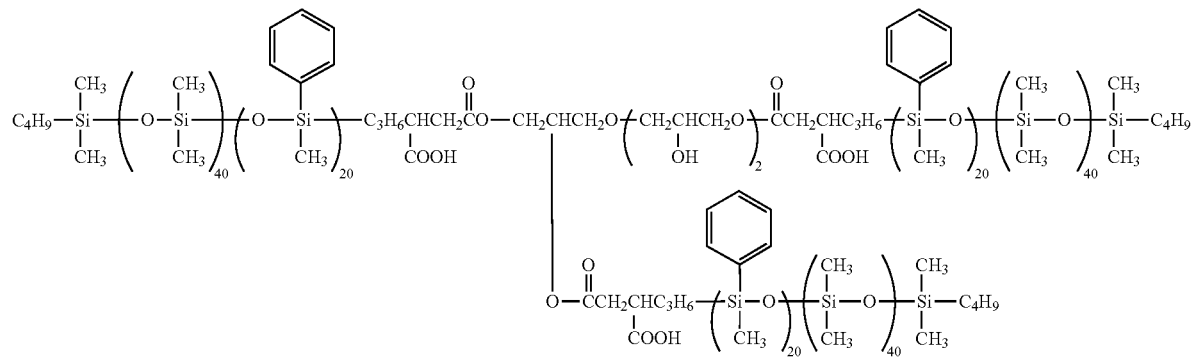

Examples 7 and 8, and Comparative Examples 1 and 2

Each W/O emulsion having composition as shown in Table 1 (blending amount is expressed with % by mass) was prepared by the method shown below.

Preparation Method:

Components 1 to 5 were mixed by agitation at 1500 rpm with a disperser mixer, and then components 6 and 7 were gradually added for emulsification.

Into a closed vessel was added 100 g of the emulsion thus obtained, and then the emulsion was allowed to stand for one week at 50° C. State of the emulsion was visually checked for evaluation according to the following standards.

Evaluation Standards:

Good: No separation

Fair: Slightly separated

Poor: Separated into two layers

TABLE 1

| | Component | Example 7 | Example 8 | Comparative Example 1 | Comparative Example 2 |
|---|---|---|---|---|---|
| 1 | Dimethylpolysiloxane (6 mm²/s) | 25 | 25 | 25 | 25 |
| 2 | Sodium salt of organopolysiloxane of Example 1 | 2 | — | — | — |
| 3 | Sodium salt of organopolysiloxane of Example 2 | — | 2 | — | — |
| 4 | Organopolysiloxane shown by following formula (Note 1) | — | — | 2 | — |
| 5 | Organopolysiloxane shown by following formula (Note 2) | — | — | — | 2 |
| 6 | 1.3-butyleneglycol | 5 | 5 | 5 | 5 |
| 7 | Purified water | 68 | 68 | 68 | 68 |
| | Stability after 1 week at 50° C. | Good | Good | Fair | Fair |

Component 2: Sodium salt of the organopolysiloxane of Example 1.

Carboxyl group of the organopolysiloxane of Example 1 was neutralized with equivalent sodium hydroxide.

Component 3: Sodium salt of the organopolysiloxane of Example 2.

Carboxyl group of the organopolysiloxane of Example 2 was neutralized with equivalent sodium hydroxide.

Note 1: Organopolysiloxane shown by the following formula.

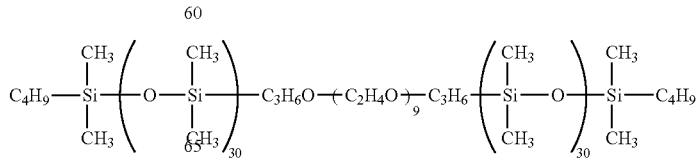

Note 2: Organopolysiloxane shown by the following formula.

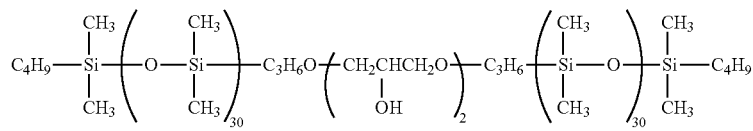

Each emulsion using respective sodium salts of the carboxyl-containing organopolysiloxanes of Examples 1 and 2 could maintain the initial emulsion state even after one week at 50° C. (Examples 7 and 8) as shown in Table 1, while emulsions of Comparative Examples 1 and 2, wherein the organopolysiloxanes not containing the carboxyl group were used, failed to show sufficient homogeneity of the oil phase thereby lacking emulsion stability.

Examples 9 and 10, and Comparative Examples 3 and 4

By using each organopolysiloxane obtained in Examples 1 and 2, a w/o foundation was prepared by the following method according to the composition shown in Table 2, and then the evaluation was conducted.

Preparation Methods:
A: Components 1 to 7 were mixed with heating, and then components 8 to 13 were mixed homogeneously.
B: Components 14, 15, and 17 were dissolved by heating.
C: With stirring, B was added gradually into A for emulsification; and then to the resulting emulsion after cooling was added component 16 to obtain a foundation.

Each foundation obtained in Examples 9 to 10 and Comparative Examples 3 to 4 was evaluated on usability, homogeneity of color tone, and cosmetic durability by the use test with the expert panel composed of 50 women.
Evaluation Standards:
  5 Points: Very good
  4 Points: Good
  3 Points: Fair
  2 Points: Slightly poor
  1 Point: Poor

TABLE 2

| | Component | Blending amount(% by mass) | | | |
|---|---|---|---|---|---|
| | | Example 9 | Example 10 | Comparative Example 3 | Comparative Example 4 |
| 1 | Decamethylcyclopentasiloxane | 45.0 | 45.0 | 45.0 | 45.0 |
| 2 | Dimethylpolysiloxane | 5.0 | 5.0 | 5.0 | 5.0 |
| 3 | Organopolysiloxane of Example 1 | 2.0 | — | — | — |
| 4 | Organopolysiloxane of Example 2 | — | 2.0 | — | — |
| 5 | Organopolysiloxane (Note 1) | — | — | 2.0 | — |
| 6 | Organopolysiloxane (Note 2) | — | — | — | 2.0 |
| 7 | Octadecyldimethylammonium salt-modified montmorillonite | 4.0 | 4.0 | 4.0 | 4.0 |
| 8 | Titanium oxide after hydrophobic treatment (Note 3) | 10.0 | 10.0 | 10.0 | 10.0 |
| 9 | Talc after hydrophobic treatment (Note 3) | 6.0 | 6.0 | 6.0 | 6.0 |
| 10 | Mica after hydrophobic treatment (Note 3) | 6.0 | 6.0 | 6.0 | 6.0 |
| 11 | Colcothar after hydrophobic treatment (Note 3) | 1.6 | 1.6 | 1.6 | 1.6 |
| 12 | Iron oxide yellow after hydrophobic treatment (Note 3) | 0.7 | 0.7 | 0.7 | 0.7 |
| 13 | Iron oxide black after hydrophobic treatment (Note 3) | 0.2 | 0.2 | 0.2 | 0.2 |
| 14 | Dipropylene glycol | 5.0 | 5.0 | 5.0 | 5.0 |
| 15 | p-oxybenzoic acid methyl ester | 0.3 | 0.3 | 0.3 | 0.3 |
| 16 | Perfume | proper amount | proper amount | proper amount | proper amount |
| 17 | Water | remaining amount | remaining amount | remaining amount | remaining amount |

(Note 1) and (Note 2): These were the same as before.

(Note 3): Hydrophobic treatment was carried by heating the powders after addition of 2% of methyl hydrogen polysiloxane.

An average point of the entire panel was taken on each evaluation item. Meaning of each word in Table 3 is as following.

Very good: average of 4.5 or more
Good: average of 3.5 or more and less than 4.5
Fair: average of 2.5 or more and less than 3.5
Slightly poor: average of 1.5 or more and less than 2.5
Poor: average of less than 1.5

TABLE 3

|  | Example 9 | Example 10 | Comparative Example 3 | Comparative Example 4 |
|---|---|---|---|---|
| Usability | Good | Very Good | Fair | Good |
| Homogeneity of color tone | Very Good | Very Good | Good | Good |
| Cosmetic durability | Very Good | Very Good | Fair | Fair |

As shown in Table 3, foundations of Comparative Examples 3 and 4 were excellent in color tone at the time of application, but poor in cosmetic durability because of poor skin affinity. On the other hand, foundations of Examples 9 and 10 were excellent in usability with a fine texture, in color tone homogeneity, in skin affinity, and in cosmetic durability, because of good pigment dispersibility.

In the following Examples, temporal stability was confirmed based on observation of no change in appearance after the cosmetic is allowed to stand in a closed vessel at 50° C. for one month.

Example 11

Eyeliner

By using the organopolysiloxane obtained in Example 1, an eyeliner was prepared by the method as shown below with the composition shown in Table 4, and then the evaluation was conducted.

TABLE 4

|  | Component | Blending amount (% by mass) |
|---|---|---|
| 1 | Octamethylcyclotetrasiloxane | remaining amount |
| 2 | Organopolysiloxane of Example 1 | 3.0 |
| 3 | Silicone resin (Note 4) | 15.0 |
| 4 | Dioctadecyldimethyl ammonium salt-modified montmorillonite | 3.0 |
| 5 | Silicone-treated iron oxide black (Note 5) | 10.0 |
| 6 | 1,3-butylene glycol | 5.0 |
| 7 | Preservative | proper amount |
| 8 | Perfume | proper amount |
| 9 | Purified water | 10.0 |

(Note 4): This silicon resin was a 50% D5 solution of a reticular silicone resin with the ratio of $Me_3SiO_{1/2}/SiO_2$ being 0.8.
(Note 5): This silicone-treated iron oxide black was prepared by heating iron oxide black with 2% by mass of methyl hydrogen polysiloxane at 150° C.

Preparation Methods:
A: Components 1 to 3 were mixed, and then component 4 was mixed therewith and dispersed homogeneously.
B: Components 5 to 7 and 9 were mixed.
C: The mixture obtained in B was added gradually for emulsification into the disperse material obtained in A; and then, to the resulting emulsion was added component 8 to obtain an eyeliner.

The eyeliner obtained by the method as shown above had light spreading properties with easy drawing, was not sticky, did not change with time and temperature, and was excellent in cosmetic durability.

Example 12

Sun Tan Cream

By using the organopolysiloxane obtained in Example 4, a sun tan cream was prepared by the method as shown below with the composition shown in Table 5, and then the evaluation was conducted.

TABLE 5

|  | Component | Blending amount (% by mass) |
|---|---|---|
| 1 | Decamethylcyclopentasiloxane | 15.0 |
| 2 | Dimethylpolysiloxane(100cs) | 5.0 |
| 3 | Silicone wax | 0.5 |
| 4 | Organopolysiloxane of Example 4 | 6.0 |
| 5 | Palmitic acid | 0.2 |
| 6 | Dimethyloctyl p-aminobenzoic acid | 0.5 |
| 7 | 4-t-butyl-4'-methoxydibenzoylmethane | 0.5 |
| 8 | Kaolin | 0.5 |
| 9 | Colcothar | 0.2 |
| 10 | Iron oxide yellow | 0.3 |
| 11 | Iron oxide black | 0.1 |
| 12 | Titanium oxide-coated mica | 1.0 |
| 13 | L-sodium glutamate | 3.0 |
| 14 | 1,3-butylene glycol | 5.0 |
| 15 | Dioctadecyldimethyl ammonium chloride | 0.1 |
| 16 | Antioxidant | proper amount |
| 17 | Preservative | proper amount |
| 18 | Perfume | proper amount |
| 19 | Purified water | remaining amount |

Preparation Methods:
A: Components 1 to 7 and 16 to 17 were dissolved by heating.
B: Component 15 and a part of component 19 were heated with stirring, and then components 8 to 12 were added thereto and dispersed.
C: Components 13 to 14 and the rest of component 19 were dissolved and then mixed with the disperse material obtained in B.
D: With stirring, the disperse material obtained in C was added gradually for emulsification into the mixture obtained in A; and then, to the resulting emulsion after cooling was added component 18 to obtain a sun tan cream.

The sun tan cream obtained by the method as mentioned above had a fine texture and light spreading properties without stickiness, and showed freshness and cleanness after its use; and in addition, there was no temporal change. In addition, the cream had good cosmetic durability.

Example 13

Cream

By using the organopolysiloxane obtained in Example 2, a cream was prepared by the method as shown below with the composition shown in Table 6, and then the evaluation was conducted.

TABLE 6

| | Component | blending amount (% by mass) |
|---|---|---|
| 1 | Decamethylcyclopentasiloxane | 20.0 |
| 2 | Glyceryl trioctanoate | 10.0 |
| 3 | Organopolysiloxane of Example 2 | 4.0 |
| 4 | Phenyldimethylstearyl ammonium chloride | 1.0 |
| 5 | Dipropylene glycol | 10.0 |
| 6 | Maltitol | 10.0 |
| 7 | Saponite | 1.5 |
| 8 | Preservative | proper amount |
| 9 | Perfume | proper amount |
| 10 | Purified water | remaining amount |

Preparation Methods:
A: Components 1 to 4 and 8 were mixed with heating.
B: Components 5 to 7 and 10 were dissolved by heating.
C: With stirring, the solution obtained in B was added gradually for emulsification into the mixture obtained in A; and then, to the resulting emulsion after cooling was added component 9 to obtain a cream.

The cream obtained by the method as shown above had light spreading properties without stickiness and greasiness, with freshness and cleanness after its use, and without temporal change.

Example 14

Sunscreen Cream

By using the organopolysiloxane obtained in Example 1, a sunscreen cream was prepared by the method as shown below with the composition shown in Table 7, and then the evaluation was conducted.

TABLE 7

| | Component | Blending amount (% by mass) |
|---|---|---|
| 1 | Decamethylcyclopentasiloxane | 20.0 |
| 2 | liquid paraffin | 10.0 |
| 3 | Organopolysiloxane of Example 1 | 4.0 |
| 4 | 4-t-butyl-4'-methoxydibenzoylmethane | 7.0 |
| 5 | Distearyldimethyl ammonium chloride | 0.8 |
| 6 | Vitamin E acetate | 0.1 |
| 7 | Ethanol | 1.0 |
| 8 | Aluminum magnesium silicate | 1.2 |
| 9 | Preservative | proper amount |
| 10 | Perfume | proper amount |
| 11 | Purified water | remaining amount |

Preparation Methods:
A: Components 1 to 6 and 9 were mixed with heating.
B: Components 7 to 8 and 11 were heated for mixing and dispersing homogenously.
C: With stirring, the dispersed material obtained in B was added gradually for emulsification into the mixture obtained in A; and then, to the resulting emulsion after cooling was added component 10 to obtain a sunscreen cream.

The sunscreen cream obtained by the method as mentioned above had a fine texture and light spreading properties without temporal change. Because the cream was not sticky, sands were not attached at all; and thus the cream could be used with extreme comfort. In addition, cosmetic durability was so good that durable UV-cut effect could be obtained.

Example 15

Eye Shadow

By using the organopolysiloxane obtained in Example 3, an eye shadow was prepared by the method as shown below with the composition shown in Table 8, and then the evaluation was conducted.

TABLE 8

| | Component | Blending amount (% by mass) |
|---|---|---|
| 1 | Decamethylcyclopentasiloxane | 15.0 |
| 2 | Dimethylpolysiloxane (6cs) | 10.0 |
| 3 | Organopolysiloxane of Example 3 | 2.0 |
| 4 | PEG(10)laurylether | 0.5 |
| 5 | Chromium oxide after silicone treatment (Note 6) | 6.2 |
| 6 | Ultramarine blue after silicone-treatment (Note 6) | 4.0 |
| 7 | Titan coated mica after silicone-treatment (Note 6) | 6.0 |
| 8 | Sodium chloride | 2.0 |
| 9 | Propylene glycol | 8.0 |
| 10 | Preservative | proper amount |
| 11 | Perfume | proper amount |
| 12 | Purified water | remaining amount |

(Note 6): Silicone-treatment was carried by heating the powders at 150° C. after addition of 3% by mass of methyl hydrogen polysiloxane.

Preparation Methods:
A: Components 1 to 4 were mixed, and then components 5 to 7 were added thereto for homogenous dispersion.
B: Components 8 to 10 and 12 were dissolved homogenously.
C: With stirring, the solution obtained in B was added gradually for emulsification into the dispersed material obtained in A; and then, to the resulting emulsion was added component 11 to obtain eye shadow.

The eye shadow obtained by the method as mentioned above had light spreading properties without greasiness and ashiness and with freshness and cleanness after its use; and in addition, good water resistance, water repellence, and durability due to anti-perspiration properties could be obtained while showing good stability without makeup deterioration because of no change by temperature and lapse of time Example 16

Lip Cream

By using the organopolysiloxane obtained in Example 4, a lip cream was prepared by the method as shown below with the composition shown in Table 9, and then the evaluation was conducted.

TABLE 9

| | Component | Blending amount (% by mass) |
|---|---|---|
| 1 | Decamethylcyclopentasiloxane | 40.0 |
| 2 | Isoparaffin (boiling point of 155° C.) | 10.0 |
| 3 | Squalane | 10.0 |
| 4 | Lanolin | 2.0 |
| 5 | Trimethylsiloxysilicate | 3.0 |

TABLE 9-continued

| | Component | Blending amount (% by mass) |
|---|---|---|
| 6 | Microcrystalline wax | 3.0 |
| 7 | Organopolysiloxane of Example 4 | 3.0 |
| 8 | Lauroylglutamic acid dibutylamide | 5.0 |
| 9 | Sodium lactate | 0.3 |
| 10 | L-sodium glutamate | 0.3 |
| 11 | Sodium hyaluronate | 0.1 |
| 12 | Sorbitol | 0.5 |
| 13 | Glycerin | 5.0 |
| 14 | Red No. 202 | proper amount |
| 15 | Menthol | proper amount |
| 16 | Preservative | proper amount |
| 17 | Perfume | proper amount |
| 18 | Purified water | remaining amount |

Preparation Methods:
A: Components 1 to 8 were mixed with heating.
B: Components 9 to 16 and 18 were dissolved by heating.
C: With stirring, the solution obtained in B was added gradually for emulsification into the mixture obtained in A; and then, to the resulting emulsion was added component 17 and then packed into a capsule to obtain a lip cream.

The solid lip cream of a water-in-oil type obtained by the method as shown above had light spreading properties without stickiness and greasiness and with good moisture, freshness, and cleanness after its use; and in addition, there was no temporal change so that the lip cream thereby obtained had good durability.

Example 17

Liquid Emulsion Foundation

By using the organopolysiloxane obtained in Example 1, a liquid emulsion foundation was prepared by the method as shown below with the composition shown in Table 10, and then the evaluation was conducted.

TABLE 10

| | Component | Blending amount (% by mass) |
|---|---|---|
| 1 | Dimethylpolysiloxane(6cs) | 5.0 |
| 2 | Decamethylcyclopentasiloxane | 15.0 |
| 3 | Squalane | 4.0 |
| 4 | neopentylglycol dioctanoate | 3.0 |
| 5 | Diglyceride of myristic acid/isostearic acid | 2.0 |
| 6 | α-monoisostearylglyceryl ether | 1.0 |
| 7 | Organopolysiloxane of Example 1 | 1.0 |
| 8 | Aluminium distearate | 0.2 |
| 9 | Titanium oxide after hydrophobic treatment (Note 7) | 5.0 |
| 10 | Sericite after hydrophobic treatment (Note 7) | 2.0 |
| 11 | Talc after hydrophobic treatment (Note 7) | 3.0 |
| 12 | Colcothar after hydrophobic treatment (Note 7) | 0.4 |
| 13 | Iron oxide yellow after hydrophobic treatment (Note 7) | 0.7 |
| 14 | Iron oxide black after hydrophobic treatment (Note 7) | 0.1 |
| 15 | Magnesium sulfate | 0.7 |
| 16 | Glycerin | 3.0 |
| 17 | Preservative | proper amount |
| 18 | Perfume | proper amount |
| 19 | Purified water | remaining amount |

(Note 7): Hydrophobic-treatment of powders was carried by treating the powders with 2% by mass of stearic acid.

Preparation Methods:
A: Components 1 to 8 were mixed with heating, and then components 9 to 14 were added thereto homogenously.
B: Components 15 to 17 and 19 were dissolved by heating.
C: With stirring, the solution obtained in B was added gradually for emulsification into the mixture obtained in A; and then, to the resulting emulsion after cooling was added component 18 to obtain a liquid emulsion foundation.

The liquid emulsion foundation obtained by the method as mentioned above had low viscosity, fine texture, and light spreading properties without stickiness and greasiness and with good moisture, freshness, and cleanness after its use; and in addition, there was no temporal change so that good cosmetic durability on a skin could be obtained.

Example 18

Transparent Gel Cosmetic

By using the organopolysiloxane obtained in Example 1, a transparent gel cosmetic was prepared by the method as shown below with the composition shown in Table 11, and then the evaluation was conducted.

TABLE 11

| | Component | Blending amount (% by mass) |
|---|---|---|
| 1 | Decamethylcyclopentasiloxane | 10.0 |
| 2 | Organopolysiloxane of Example 1 | 10.0 |
| 3 | 1,3-butylene glycol | 10.0 |
| 4 | Polyethylene glycol 400 | 9.0 |
| 5 | 2-hydroxyoctanonic acid | 1.0 |
| 6 | Sorbitol(70% aqueous solution) | 10.0 |
| 7 | Citric acid | proper amount |
| 8 | Sodium citrate | proper amount |
| 9 | Preservative | proper amount |
| 10 | Perfume | proper amount |
| 11 | Purified water | remaining amount |

Preparation Methods:
A: Components 3 to 11 were dissolved homogenously.
B: Components 1 to 2 were mixed homogeneously.
C: With stirring, the solution obtained in A was added gradually for emulsification into the mixture obtained in B to obtain a transparent gel cosmetic.

The transparent gel cosmetic obtained by the method as mentioned above had light spreading properties without stickiness and greasiness and with good moisture, freshness, and cleanness after its use; and in addition, there was no temporal change with good skin affinity.

Example 19

Sunscreen Lotion

By using the organopolysiloxane obtained in Example 2, a sunscreen lotion was prepared by the method as shown below with the composition shown in Table 12, and then the evaluation was conducted.

TABLE 12

| | Component | Blending amount (% by mass) |
|---|---|---|
| 1 | Decamethylcyclopentasiloxane | 14.0 |
| 2 | Organopolysiloxane of Example 2 | 10.0 |
| 3 | Squalane | 1.5 |
| 4 | Octyl p-methoxycinnamate | 3.0 |
| 5 | hydrophobizing-treated ultra-fine titanium oxide powders (Note 8) | 2.0 |
| 6 | 1,3-butylene glycol | 10.0 |
| 7 | Sodium chloride | 2.0 |
| 8 | L-proline | 0.1 |
| 9 | 2-hydroxyoctanonic acid | 1.0 |
| 10 | 2-hydroxypropanoic acid | 5.0 |
| 11 | Sodium hydroxide | proper amount |
| 12 | Preservative | proper amount |
| 13 | Perfume | proper amount |
| 14 | Purified water | remaining amount |

(Note 8): Titan TTO-V-4 (manufactured by Ishihara Sangyo Kaisha, Ltd.) was used as the hydrophobizing-treated ultra-fine titanium oxide powders.

Preparation Methods:
A: Components 6 to 14 were dissolved homogenously.
B: Components 1 to 4 were mixed; and then component 5 was added thereto homogeneously.
C: With stirring, B was added gradually for emulsification into A to obtain a sunscreen lotion.

The sunscreen lotion obtained by the method as mentioned above had light spreading properties without stickiness and greasiness and with good moisture, freshness, and cleanness after its use; and in addition, there was no temporal change with good skin affinity.

The lotion was excellent in a sunscreen effect as well.

Example 20

Milky Lotion

By using the organopolysiloxane obtained in Example 1, a milky lotion was prepared by the method as shown below with the composition shown in Table 13, and then the evaluation was conducted.

TABLE 13

| | Component | blending amount (% by mass) |
|---|---|---|
| 1 | Decamethylcyclopentasiloxane | 18.0 |
| 2 | Dimethylpolysiloxane(6cs) | 6.0 |
| 3 | Squalane | 5.0 |
| 4 | Neopentylglycol dioctanoate | 3.0 |
| 5 | α-monooleyl glyceryl ether | 1.0 |
| 6 | Organopolysiloxane of Example 1 | 2.0 |
| 7 | Aluminum distearate | 0.2 |
| 8 | Magnesium sulfate | 0.7 |
| 9 | Glycerin | 5.0 |
| 10 | Preservative | proper amount |
| 11 | Perfume | proper amount |
| 12 | Purified water | remaining amount |

Preparation Methods:
A: Components 1 to 7 were mixed with heating.
B: Components 8 to 10 and 12 were dissolved by heating.
C: With stirring, the solution obtained in B was added gradually for emulsification into the mixture obtained in A; and then, to the resulting emulsion after cooling was added component 11 to obtain a milky lotion.

The milky lotion obtained by the method as mentioned above had low viscosity, fine texture, and light spreading properties without stickiness and greasiness and with good moisture, freshness, and cleanness after its use; and in addition, there was no temporal change. Cosmetic durability on a skin was good as well.

Example 21

Sunscreen Cream

By using the organopolysiloxane obtained in Example 3, a sunscreen cream was prepared by the method as shown below with the composition shown in Table 14, and then the evaluation was conducted.

TABLE 14

| | Component | blending amount (% by mass) |
|---|---|---|
| 1 | Decamethylcyclopentasiloxane | 18.0 |
| 2 | Methylphenylpolysiloxane | 2.0 |
| 3 | Liquid paraffin | 1.5 |
| 4 | Organopolysiloxane of Example 3 | 4.0 |
| 5 | Oactyl p-methoxycinnamate | 5.0 |
| 6 | 1,3-butylene glycol | 4.0 |
| 7 | Sodium chloride | 1.0 |
| 8 | Preservative | proper amount |
| 9 | Perfume | proper amount |
| 10 | Purified water | remaining amount |

Preparation Methods:
A: Components 1 to 5 were mixed with heating.
B: Components 6 to 8 and 10 were dissolved by heating.
C: With stirring, the solution obtained in B was added gradually for emulsification into the mixture obtained in A; and then, to the resulting emulsion after cooling was added component 9 to obtain a sunscreen cream.

The sunscreen cream obtained by the method as mentioned above had a fine texture and light spreading properties with moisture and freshness and without greasiness, stickiness, and temporal change. In addition, the sunscreen cream thus obtained was excellent in water resistance and anti-perspiration properties, and thus, cosmetic durability was excellent as well so that durable UV-cut effect could be obtained.

Example 22

Liquid Foundation

By using the organopolysiloxane obtained in Example 1, a liquid foundation was prepared by the method as shown below with the composition shown in Table 15, and then the evaluation was conducted.

TABLE 15

| | Component | Blending amount (% by mass) |
|---|---|---|
| 1 | Decamethylcyclopentasiloxane | 16.0 |
| 2 | Dimethylpolysiloxane (6cs) | 8.0 |
| 3 | Oactyl p-methoxycinnamate | 3.0 |
| 4 | 12-hydroxystearic acid | 1.0 |
| 5 | Fluorine-modified silicone (Note 9) | 15.0 |
| 6 | Organopolysiloxane of Example 1 | 5.0 |
| 7 | Silicone resin spherical powders (Note 10) | 3.0 |
| 8 | Titanium oxide particle after fluorine compound-treatment (Note 11) | 8.0 |
| 9 | Titanated mica after fluorine compound-treatment (Note 11) | 1.0 |
| 10 | Titanium oxide after fluorine compound-treatment (Note 11) | 5.0 |
| 11 | Colcothar after fluorine compound-treatment (Note 11) | 0.9 |
| 12 | Iron oxide yellow after fluorine compound-treatment (Note 11) | 2.0 |
| 13 | Iron oxide black after fluorine compound-treatment (Note 11) | 1.0 |
| 14 | Ethanol | 15.0 |
| 15 | Glycerin | 3.0 |
| 16 | Magnesium sulfate | 1.0 |
| 17 | Preservative | proper amount |
| 18 | Perfume | proper amount |
| 19 | Purified water | remaining amount |

(Note 9): FL-100 (manufactured by Shin-Etsu Chemical Co., Ltd.) was used as the fluorine-modified silicone.
(Note 10): KMP 590 (manufactured by Shin-Etsu Chemical Co., Ltd.) was used as the silicone resin spherical powders.
(Note 11): fluorine compound-treatment was conducted to cover 5% of the powders with a diethanolamine salt of a perfluoroalkyl ethyl phosphate.

Preparation Methods:

A: Components 7 to 13 were mixed homogeneously.

B: Components 1 to 6 were mixed with heating at 70° C. and then the mixture obtained in A was added thereto; the resulting mixture was mixed and dispersed homogenously.

C: Components 14 to 17 and 19 were heated at 40° C. to obtain a solution, which was then gradually added for emulsification into the dispersed material obtained in B; and then, to the resulting emulsion after cooling was added component 18 to obtain a liquid foundation.

The liquid foundation obtained by the method as mentioned above had light spreading properties with freshness and without stickiness. There was no temporal change, either.

Example 23

Milky Lotion

By using the organopolysiloxane obtained in Example 1, a milky lotion was prepared by the method as shown below with the composition shown in Table 16, and then the evaluation was conducted.

TABLE 16

| | Component | blending amount (% by mass) |
|---|---|---|
| 1 | Decamethylcyclopentasiloxane | 15.0 |
| 2 | Methylphenylpolysiloxane | 5.0 |
| 3 | Squalene | 5.0 |
| 4 | Pentaerythritol tetra-2-ethyl hexanoate | 5.0 |
| 5 | Organopolysiloxane of Example 1 | 3.0 |
| 6 | Spherical powders of organopolysiloxane elastomer (Note 12) | 2.0 |
| 7 | Hydrophobized silica (Note 13) | 0.5 |
| 8 | Magnesium ascorbic acid phosphate | 1.0 |
| 9 | Sodium chloride | 1.0 |
| 10 | Polyethylene glycol 11000 | 1.0 |
| 11 | Propylene glycol | 8.0 |
| 12 | Preservative | proper amount |
| 13 | Perfume | proper amount |
| 14 | Purified water | remaining amount |

(Note 12): KMP594 (manufactured by Shin-Etsu Chemical Co., Ltd.) was used as the spherical powders of organopolysiloxane elastomer.
(Note 13): Aerosil R972 (manufactured by Nippon Aerosil Co., Ltd.) was used as the hydrophobized silica.

Preparation Methods:

A: Components 1 to 5 were mixed homogeneously, and then components 6 to 7 were added thereto; and the resulting mixture was dispersed homogenously.

B: Components 8 to 10 were added for dissolution into component 14, and then a mixture of components 11 and 12 was added thereto.

C: The mixture obtained in B was gradually added for emulsification into the dispersed material obtained in A; and then, to the resulting emulsion after cooling was added component 13 to obtain a milky lotion.

The milky lotion obtained by the method as mentioned above had light spreading properties without stickiness and tackiness; and there was no temporal change, either.

Example 24

Moisture Cream

By using the organopolysiloxane obtained in Example 1, a moisture cream was prepared by the method as shown below with the composition shown in Table 17, and then the evaluation was conducted.

TABLE 17

| | Component | Blending amount (% by mass) |
|---|---|---|
| 1 | Decamethylcyclopentasiloxane | 10.0 |
| 2 | Methylphenylpolysiloxane | 3.0 |
| 3 | Liquid paraffin | 5.0 |

TABLE 17-continued

| | Component | Blending amount (% by mass) |
|---|---|---|
| 4 | Pentaerythritol tetra-2-ethyl hexanoate | 3.0 |
| 5 | Cetyl 2-ethylhexanoate | 5.0 |
| 6 | Organopolysiloxane of Example 1 | 1.0 |
| 7 | Spherical powders of organopolysiloxane elastomer (Note 14) | 2.5 |
| 8 | Hydrophobized silica (Note 15) | 2.0 |
| 9 | Zinc stearate | 2.0 |
| 10 | Vitamin E acetate | 3.0 |
| 11 | Polyethylene glycol 400 | 1.0 |
| 12 | Sodium lactate | 1.0 |
| 13 | 1,3-butylene glycol | 5.0 |
| 14 | Preservative | proper amount |
| 15 | Perfume | proper amount |
| 16 | Purified water | remaining amount |

(Note 14): KMP594 (manufactured by Shin-Etsu Chemical Co., Ltd.) was used as the spherical powders of organopolysiloxane elastomer.
(Note 15): Aerosil R972 (manufactured by Nippon Aerosil Co., Ltd.) was used as the hydrophobized silica.

Preparation Methods:
A: Components 1 to 6 and 9 to 10 were mixed homogeneously, and then components 7 to 8 were added thereto; and the resulting mixture was dispersed homogenously.
B: Components 11 to 14 and 16 were mixed and dissolved.
C: The solution obtained in B was gradually added for emulsification into the mixture obtained in A; and then, to the resulting emulsion after cooling was added component 15 to obtain a moisture cream.

The moisture cream obtained by the method as mentioned above had light spreading properties without stickiness; and there was no temporal change, either.

Example 25

Eyeliner

By using the organopolysiloxane obtained in Example 2, an eyeliner was prepared by the method as shown below with the composition shown in Table 18, and then the evaluation was conducted.

TABLE 18

| | Component | Blending amount (% by mass) |
|---|---|---|
| 1 | Decamethylcyclopentasiloxane | 22.0 |
| 2 | Dimethylpolysiloxane(6cs) | 5.0 |
| 3 | Iron oxide black after silicone treatment | 20.0 |
| 4 | Vitamin E acetate | 0.2 |
| 5 | Jojoba oil | 2.0 |
| 6 | Bentonite | 3.0 |
| 7 | Organopolysiloxane of Example 2 | 2.0 |
| 8 | Ethanol | 10.0 |
| 9 | 1,3-butylene glycol | 10.0 |
| 10 | Preservative | proper amount |
| 11 | Perfume | proper amount |
| 12 | Purified water | remaining amount |

Preparation Methods:
A: Components 1 to 2 and 4 to 7 were mixed homogeneously, and then component 3 was added thereto; and the resulting mixture was dispersed homogenously.
B: Components 8 to 10 and 12 were mixed.
C: The mixture obtained in B was gradually added for emulsification into the disperse material obtained in A; and then, to the resulting emulsion after cooling was added component 11 to obtain an eyeliner.

The eyeliner obtained by the method as shown above had light spreading properties with easy drawing and did not change with time. In addition, the eyeliner showed excellent water resistance and anti-perspiration properties on a skin, thereby showing excellent cosmetic durability.

Example 26

Sun-Cut Cream

By using the organopolysiloxane obtained in Example 1, a sun-cut cream was prepared by the method as shown below with the composition shown in Table 19, and then the evaluation was conducted.

TABLE 19

| | Component | Blending amount (% by mass) |
|---|---|---|
| 1 | Decamethylcyclopentasiloxane | 17.5 |
| 2 | KP545 (Note 16) | 12.0 |
| 3 | Glyceryl triisooctanoate | 5.0 |
| 4 | Octyl p-methoxycinnamate | 6.0 |
| 5 | KSG210 (Note 17) | 5.0 |
| 6 | Organopolysiloxane of Example 1 | 1.0 |
| 7 | Zinc oxide after lipophilic treatment | 20.0 |
| 8 | Sodium chloride | 0.5 |
| 9 | 1,3-butylene glycol | 2.0 |
| 10 | Preservative | proper amount |
| 11 | Perfume | proper amount |
| 12 | Purified water | remaining amount |

(Note 16): KP 545 (manufactured by Shin-Etsu Chemical Co., Ltd.) was used as the acryl silicone.
(Note 17): KSG 210 (manufactured by Shin-Etsu Chemical Co., Ltd.) was used as the silicone gel.

Preparation Methods:
A: Component 2 and a part of component 1 were mixed homogeneously, and then component 7 was added thereto; and the resulting mixture was dispersed by a bead mill.
B: The rest of component 1 and components 3 to 6 were mixed homogeneously.
C: Components 8 to 10 and 12 were mixed and dissolved.
D: The solution obtained in C was added for emulsification into the mixture obtained in B; and then, to the resulting emulsion were added A and component 11 to obtain a sun-cut cream.

The sun-cut cream obtained by the method as shown above had light spreading properties with contact-feeling and without stickiness. There was no temporal change, and durable UV-cut properties on a skin could be obtained.

Example 27

O/W Hand Cream

By using the organopolysiloxane obtained in Example 4, an o/w hand cream was prepared by the method as shown below with the composition shown in Table 20, and then the evaluation was conducted.

TABLE 20

| | Component | Blending amount (% by mass) |
|---|---|---|
| 1 | KP545 (Note 18) | 10.0 |
| 2 | KSG16 (Note 19) | 2.0 |
| 3 | Isoparaffin | 5.0 |
| 4 | Petrolatum | 5.0 |
| 5 | Glyceryl triisooctanoate | 3.0 |
| 6 | Organopolysiloxane of Example 4 | 0.5 |
| 7 | Polyoxyethylenesorbitan monooleate | 1.0 |
| 8 | Sepigel 305 (Note 20) | 2.0 |
| 9 | 1,3-butylene glycol | 5.0 |
| 10 | Glycerin | 5.0 |
| 11 | Preservative | proper amount |
| 12 | Perfume | proper amount |
| 13 | Purified water | remaining amount |

(Note 18): KP 545 (manufactured by Shin-Etsu Chemical Co., Ltd.) was used as the acryl silicone.
(Note 19): KSG 16 (manufactured by Shin-Etsu Chemical Co., Ltd.) was used as the silicone gel.
(Note 20): Seppi Gel 305 (manufactured by SEPPIC S. A.) was used.

Preparation Methods:
A: Components 1 to 7 were mixed homogeneously.
B: Components 8 to 11 and 13 were mixed homogeneously.
C: The solution obtained in B was added for emulsification into the mixture obtained in A; and then, to the resulting emulsion was added component 12 to obtain an o/w hand cream.

The hand cream obtained by the method as shown above had light spreading properties with excellent contact-feeling thereby effectively protecting a skin during wet work. There was no temporal change either.

Example 28

O/W Hand Cream

By using the organopolysiloxane obtained in Example 1, an o/w hand cream was prepared by the method as shown below with the composition shown in Table 21, and then the evaluation was conducted.

TABLE 21

| | Component | Blending amount (% by mass) |
|---|---|---|
| 1 | KP545 (Note 21) | 10.0 |
| 2 | KP561P (Note 22) | 8.0 |
| 3 | Cetanol | 1.0 |
| 4 | Glyceryl triisostearate | 5.0 |
| 5 | Stearic acid | 3.0 |
| 6 | Glyceryl monostearate | 1.5 |
| 7 | Organopolysiloxane of Example 1 | 0.7 |
| 8 | Sorbitan Sesquioleate | 0.5 |
| 9 | Polyoxyethylenesorbitan monooleate | 1.0 |
| 10 | Sodium hydroxide (1% aqueous solution) | 10.0 |
| 11 | 1,3-butylene glycol | 5.0 |
| 12 | Preservative | proper amount |
| 13 | Perfume | proper amount |
| 14 | Purified water | remaining amount |

(Note 21): KP 545 (manufactured by Shin-Etsu Chemical Co., Ltd.) was used as the acryl silicone.
(Note 22): KP 561P (manufactured by Shin-Etsu Chemical Co., Ltd.) was used as the stearyl-modified acryl silicone.

Preparation Methods:
A: Components 1 to 9 were mixed and dissolved with heating.
B: Components 10 to 12 and 14 were mixed with heating.
C: The mixture obtained in B was added for emulsification into the solution obtained in A; and then, to the resulting emulsion after cooling was added component 13 to obtain an o/w hand cream.

The hand cream obtained by the method as shown above had light spreading properties with excellent contacting feeling and without stickiness, thereby effectively protecting a skin during wet work. There was no temporal change, either.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:

1. An organopolysiloxane of general formula (1);

$$R^1-\underset{\underset{R^1}{|}}{\overset{\overset{R^1}{|}}{Si}}-\left(O-\underset{\underset{R^1}{|}}{\overset{\overset{R^1}{|}}{Si}}\right)_m-C_3H_6CHCH_2\underset{\underset{COOM}{|}}{CO}-Y-\underset{\underset{COOM}{|}}{OCCH_2CHC_3H_6}- \quad (1)$$

$$\left(-\underset{\underset{R^1}{|}}{\overset{\overset{R^1}{|}}{Si}}-O-\right)_m\underset{\underset{R^1}{|}}{\overset{\overset{R^1}{|}}{Si}}-R^1$$

wherein each $R^1$ independently is selected from a group consisting of an alkyl group having 1 to 30 carbon atoms, a fluorine-substituted alkyl group having 1 to 30 carbon atoms, an aryl group having 6 to 30 carbon atoms, and an aralkyl group having 6 to 30 carbon atoms; Y is a polyhydric alcohol compound residue; M is a hydrogen atom, an alkaline metal atom, an ammonium ion, or an alkylammonium ion; and reference character m is an integer of 0 to 300.

2. The organopolysiloxane according to claim 1, wherein the polyhydric alcohol compound residue Y is a (poly)oxyalkylene residue, a (poly)glycerine residue, or a polyglycerine alkyl ester residue.

3. The organopolysiloxane according to claim 1, wherein the organopolysiloxane is general formula (2);

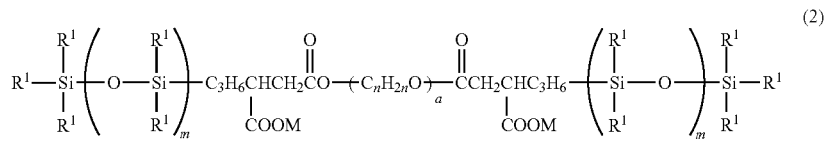
(2)

wherein $R^1$, M, and reference character m has the same meaning as in claim 1; reference character n is an integer of 2 to 6 and reference character a is an integer of 1 to 50.

4. The organopolysiloxane according to claim 1, wherein the organopolysiloxane is general formula (3);

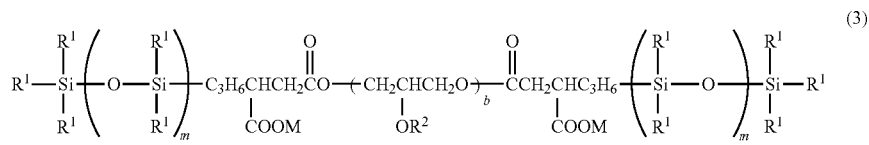
(3)

wherein $R^1$, M, and reference character m has the same meaning as in claim 1; each of $R^2$ is independently a hydrogen atom or is general formula (4); reference character b is an integer of 1 to 10;

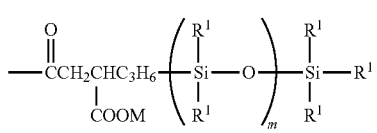
(4)

wherein $R^1$, M, and reference character m has the same meaning as in claim 1.

5. A cosmetic containing the organopolysiloxane according to claim 1 in a range between 0.1 and 40% by mass based on the total mass.

6. The cosmetic according to claim 5, wherein the cosmetic further contains water and is in a form of an emulsion.

7. The cosmetic according to claim 5, wherein the cosmetic further contains at least one or more of a silicone oil, an ester oil, and a glyceride oil, and is in a form of a non-aqueous emulsion.

8. The cosmetic according to claim 5, wherein the cosmetic further contains powders and is in a form of a liquid, a paste, or a solid, wherein the powders are dispersed.

* * * * *